(12) United States Patent
Funamara et al.

(10) Patent No.: US 7,581,561 B2
(45) Date of Patent: Sep. 1, 2009

(54) CONNECTOR

(75) Inventors: Shigeaki Funamara, Fukuroi (JP); Ichiro Kitani, Fukuroi (JP)

(73) Assignee: Tyco Healthcare Group LP, Mansfield, MA (US)

(*) Notice: Subject to any disclaimer, the term of this patent is extended or adjusted under 35 U.S.C. 154(b) by 320 days.

(21) Appl. No.: 11/673,102

(22) Filed: Feb. 9, 2007

(65) Prior Publication Data

US 2007/0175485 A1  Aug. 2, 2007

(51) Int. Cl.
*F16K 11/085* (2006.01)
(52) U.S. Cl. .............. 137/625.47; 137/625.4; 251/149.1; 604/248
(58) Field of Classification Search .......... 251/149.1, 251/149.6; 137/625.4, 625.41, 625.46, 625.47; 604/248, 256, 905
See application file for complete search history.

(56) References Cited

U.S. PATENT DOCUMENTS

| | | | |
|---|---|---|---|
| 5,135,026 A * | 8/1992 | Manska | 137/555 |
| 5,360,413 A * | 11/1994 | Leason et al. | 604/249 |
| 5,509,433 A | 4/1996 | Paradis | |
| 5,836,923 A * | 11/1998 | Mayer | 604/246 |
| 6,171,287 B1 * | 1/2001 | Lynn et al. | 604/256 |
| 2002/0082586 A1 | 6/2002 | Finley et al. | |
| 2003/0105452 A1 | 6/2003 | Mayer | |

FOREIGN PATENT DOCUMENTS

| | | |
|---|---|---|
| EP | 0629418 A2 | 12/1994 |
| JP | 08-206230 | 8/1996 |
| JP | 2003-159336 | 6/2003 |
| WO | 2005/107847 A1 | 7/2007 |

OTHER PUBLICATIONS

Extended European Search Report for Application No. 06023658.5—1526 dated Mar. 21, 2007.

* cited by examiner

*Primary Examiner*—John K Fristoe, Jr.

(57) ABSTRACT

A connector, for example a Luer connector, has a sealing element such that when a connection is made to the connector, the sealing element is displaced into the connector, opening a fluid flow channel through the connector. The sealing member may include a slit on a lower surface thereof to ease the displacement of the sealing member.

21 Claims, 33 Drawing Sheets

CONNECTOR

FIELD OF THE INVENTION

The present invention generally relates to a closure for a connector, a connector and a fluid through-flow connector.

BACKGROUND OF THE INVENTION

In medical institutions, liquid transport is often needed, such as an infusion, transfusion, artificial dialysis, blood collection, etc. Tubes are used to transport various types of liquids. A connector controls the tubes, merging multiple types of liquids or blocking the flow as needed. Said connector is set halfway on the tube, and a mixer for mixing in other medicine solutions is attached to the tube, and various other applications are adopted for the tube. For example, the connector may have the function of a switching valve, and the valve is used as a 3-way valve that can control the feeding of liquids from multiple flow channels. The connector is attached at the terminal of a medicine solution tube, and it usually blocks the feeding of the liquid from said medicine solution tube, and it is opened only when needed for feeding the liquid. That is, the connector is used as a normally OFF valve.

Usually, the connector has a housing that forms a flow channel space for the flow of the medicine solution or other liquid. The housing has a connecting port connected to the flow channel. The flow channel is connected through the connecting port to the flow channel space for the flow of the medicine solution. Also, in the housing, an opening portion is formed for feeding the liquid to be fed from the outside. The Luer syringe portion is inserted in the opening portion, and the medicine solution or the like is fed through the opening portion into the flow channel space.

However, for the connector of an opened system with nothing attached to the opening portion, when the Luer syringe portion is not inserted while the flow channel space is normally connected to the outside, the medicine solution may spill out of the flow channel space. Also, bacteria may reproduce in the portion attached to the medicine solution near the opening portion. Consequently, in the recent years, a normally closed type valve member is attached to the opening portion, and, when the Luer syringe portion is not inserted, the opening portion is blocked liquid tight. Such connector of the blocked system is often in use.

The connector of the blocked system usually has a slit formed on the valve member attached to the opening portion (see Japanese Kokai Patent Application No. 2003 159336 and Japanese Kokai Patent Application No. Hei 8[1996]206230). Then, in the normal state (when the Luer syringe portion is not inserted, and no liquid is fed), this slit is closed. On the other hand, when liquid feeding is performed, the Luer syringe portion is inserted in the slit. Then, the slit is opened, and the Luer syringe portion is exposed to the flow channel space inside the housing. As the liquid to be fed is injected in this state, the liquid is injected into the flow channel space, and the liquid is fed. After end of feeding of the liquid, the Luer syringe portion is pulled out of the slit. As a result, the slit is once again closed, and the opening portion is blocked.

For the valve member used in the conventional connector of the blocked system, said through slit is formed, and the Luer syringe portion is inserted via said slit. Consequently, as the slit is opened/closed repeatedly, the slit portion degrades. When the slit portion degrades, the slit cannot be well closed. In this state, the advantage of the connector of the blocked system cannot be well displayed, and the liquid may leak out of the flow channel space. Also, bacteria may reproduce at the periphery of the slit.

SUMMARY OF THE INVENTION

In one aspect of the present invention, a closure is for a connector having a housing. The housing has an opening portion opened to the outside, a connecting port connected to a tube and a flow channel space that allows flow of liquid through the connecting port. The closure generally comprises a valve member for attachment to the opening portion and for allowing a liquid from outside to flow into the flow channel space after opening of the valve member. The valve member comprises a main body portion that seals the opening portion liquid tight and can be moved to the side of the flow channel space under the pressing force from the outside. The main body portion has an outer surface facing the outside and an inner surface facing the flow channel space while the opening portion is blocked liquid tight. A supporting portion is connected to the main body portion and is engaged to the housing. The supporting portion has an elastic force that acts on the main body portion when the main body portion moves to the side of the flow channel space under the pressing force from the outside. A connecting surface formed on the outer surface of the main body portion is connected to the flow channel space when the main body portion is pressed into the side of the flow channel space under the pressing force from outside.

In another aspect, a connector generally comprises a housing having an opening portion opened to the outside, a connecting port connected to a tube and a flow channel space that allows flow of liquid through the connecting port. A valve member for attachment to the opening portion allows a liquid from outside to flow into the flow channel space after opening of the valve member. The valve member comprises a main body portion that seals the opening portion liquid tight and can be moved to the side of the flow channel space under the pressing force from the outside. The main body portion has an outer surface facing the outside and an inner surface facing the flow channel space while the opening portion is blocked liquid tight. A supporting portion is connected to the main body portion and is engaged to the housing. The supporting portion has an elastic force that acts on the main body portion when the main body portion moves to the side of the flow channel space under the pressing force from the outside. A connecting surface formed on the outer surface of the main body portion is connected to the flow channel space when the main body portion is pressed into the side of the flow channel space under the pressing force from outside.

In yet another aspect, a fluid through-flow connector comprises at least one connection port. The connection port comprises a connection port housing having an inner surface defining an inner volume and an outer surface. A sealing member has an inner portion extending within the inner volume and at least one outer portion extending externally of the housing. The inner portion includes an inner slit extending from a lower surface of the inner portion. The sealing member is of an elastically deformable material. The sealing member is arranged such that it is deformable from a first closed state in which the sealing member is arranged in a fluid sealing configuration to a second open state in which the sealing member is arranged in a fluid non-sealing configuration and in which the inner portion is displaced into the inner volume and in which the at least one outer portion exerts a restoring force on the inner portion urging the inner portion to return to the first closed state. The deformation from the first closed state to the second open state being caused by the making of a connection to the connection port.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
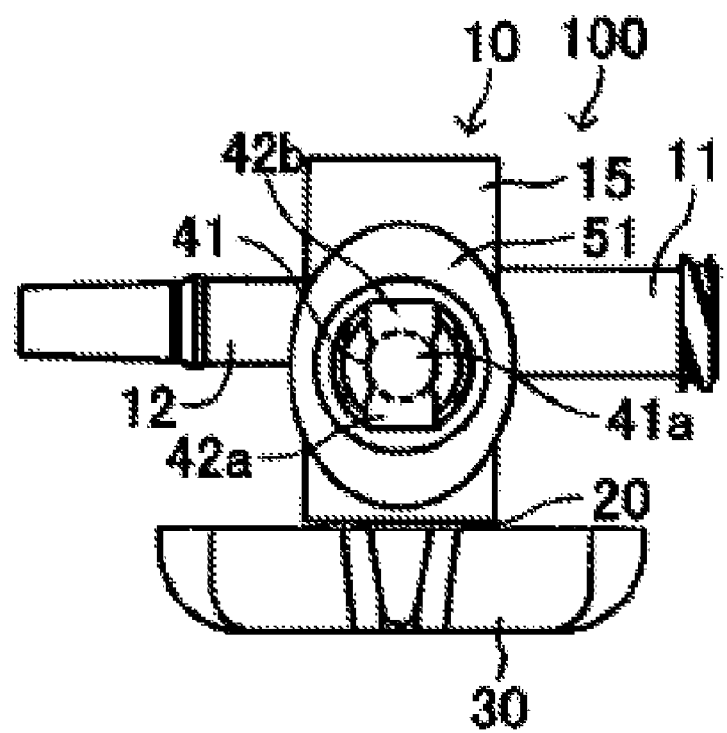
FIG. 1 is a plan view of the 3-way valve in Embodiment 1 of the present invention.
Figure 2:
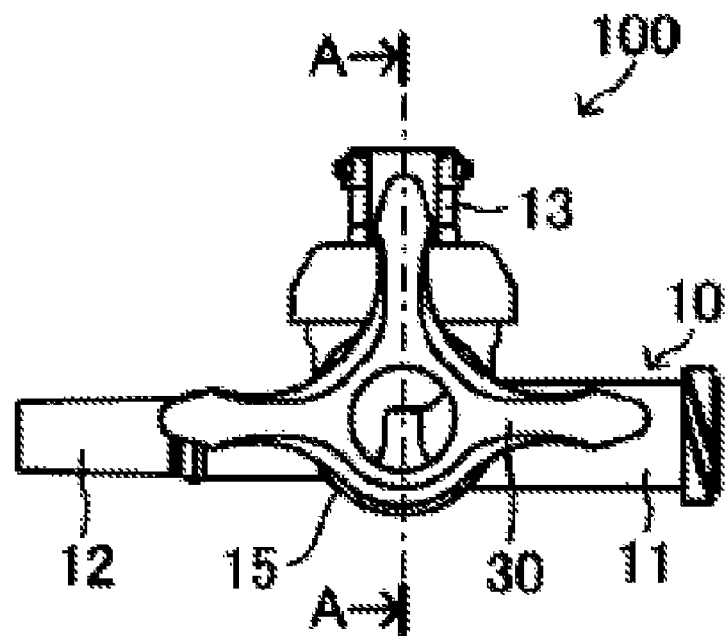
FIG. 2 is a front view of the 3-way valve in Embodiment 1 of the present invention.
Figure 3:
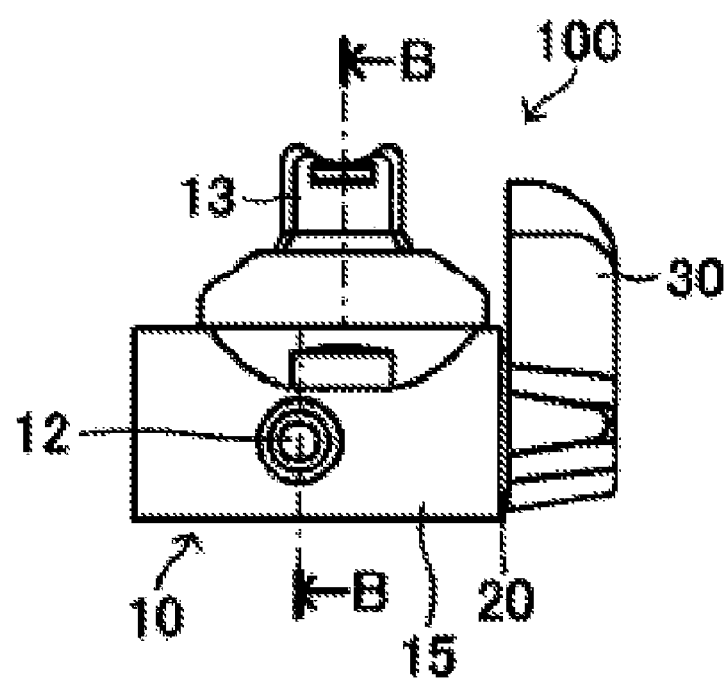
FIG. 3 is a left side view of the 3-way valve in Embodiment 1 of the present invention.

In the following, a detailed explanation will be given regarding embodiments of the connector of the present invention with reference to figures. First of all, as Embodiment 1, the connector of the present invention is used as a 3-way valve. FIG. 1 is a plan view of a 3-way valve which is concerned in Embodiment 1 of the present invention. FIG. 2 is a front view, and FIG. 3 is a left side view of what shown in FIG. 2. As can be seen from these figures, said 3-way valve (100) is composed of housing (10), valve body (20), and holding portion (30). Said valve body (20) and holding portion (30) are formed integrally, and valve body (20) is mounted in housing (10).

Said housing (10) is composed of cylindrical part (15) and three branching tubes mounted on said cylindrical part (15), that is, first branching tube (11), second branching tube (12) and third branching tube (13). In these branching tubes, the respective branching flow channels (first branching flow channel (11a), second branching flow channel (12a) and third branching flow channel (13a)) are formed. The various branching flow channels are opened on the inner wall of cylindrical part (15). Also, in this embodiment, the materials that can be used in forming housing (10) include polycarbonate (PC), as well as polypropylene (PP), polyethylene terephthalate (PET), and other resin materials.

Figure 4:
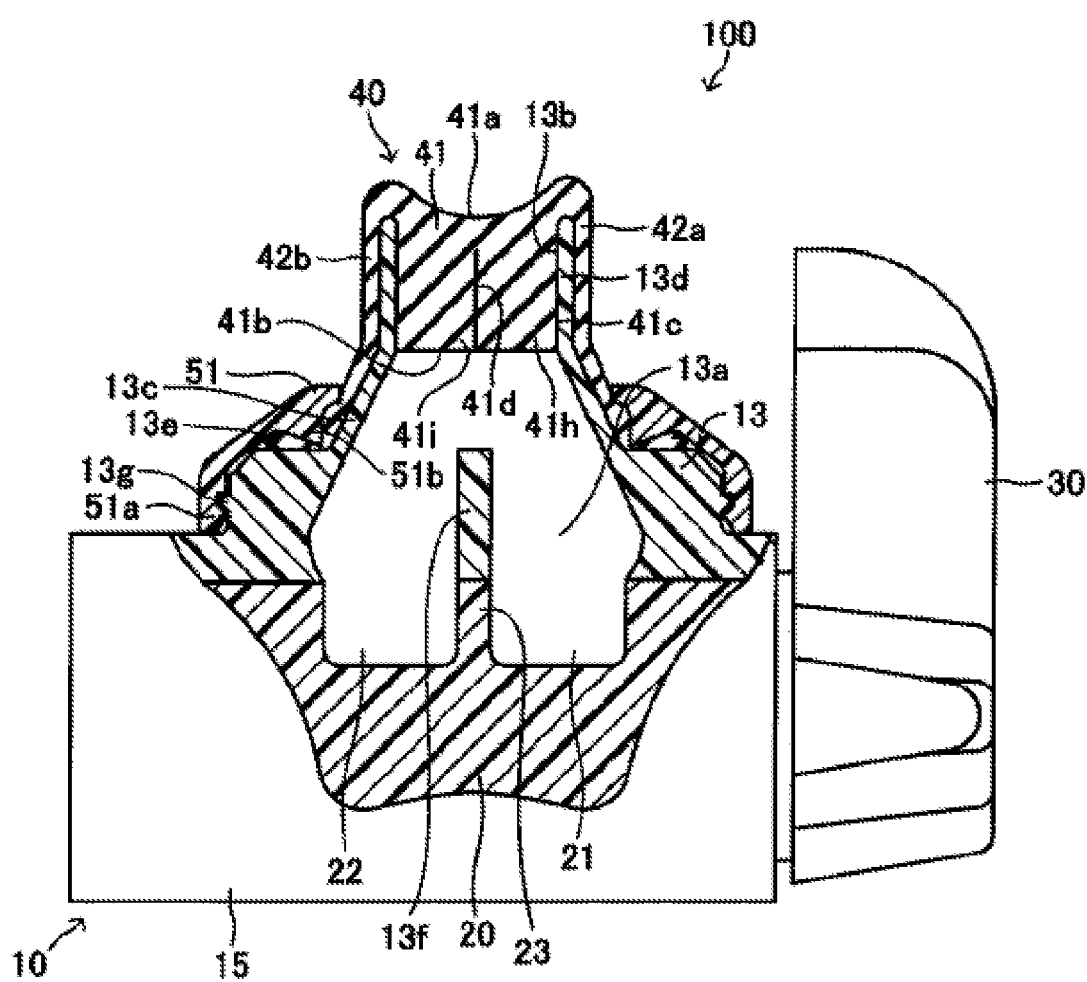
FIG. 4 is a partial cross sectional view taken across A-A in FIG. 2.
Figure 5:
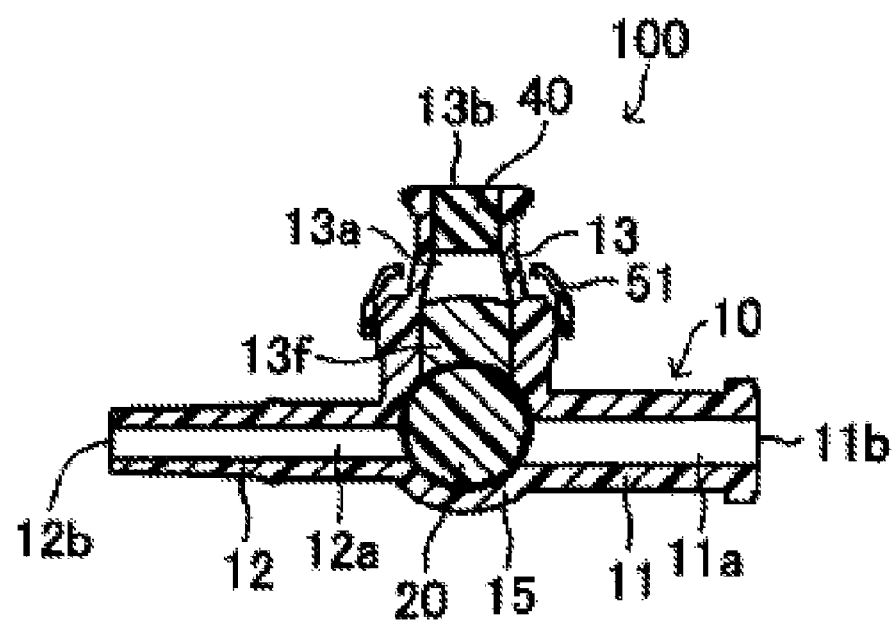
FIG. 5 is a cross sectional view taken across B-B in FIG. 3.

FIG. 4 is a partial cross sectional view taken across A-A in FIG. 2, and FIG. 5 is a cross sectional view taken across B-B in FIG. 3. As shown in FIG. 5, valve body (20) is fitted in a rotatable way on the inner periphery of cylindrical part (15) of housing (10). Also, as shown in FIG. 4, on the outer periphery of valve body (20), two grooves (21), (22) are formed. Also, holding portion (30) is mounted on one end portion of valve body (20). Said holding portion (30) has three arm portions, and it rotates integrally with valve body (20). Consequently, by rotating holding portion (30), valve body (20) is also rotated on the inner periphery of cylindrical part (15). By rotation of valve body (20), the setting state of grooves (21), (22) formed on the outer periphery of valve body (20) is changed. By changing the setting state of grooves (21), (22) to any of various states, it is possible to switch ON/OFF the branching flow channels formed in the various branching tubes.

In this embodiment, valve body (20) and holding portion (30) are integrally formed. The material is polyethylene (PE). However, one may also make use of other resins, such as polyoxymethylene (POM), polypropylene (PP), etc.

As can be seen from FIG. 5, first branching tube (11) is connected to the right-hand side of cylindrical part (15). Opening portion (11b) of said first branching flow channel (11a) is opened to the right-hand side shown in the figure. Also, second branching tube (12) is connected to the left-hand side of cylindrical part (15), and opening portion (12b) of second branching flow channel (12a) is opened to the left-hand side shown in the figure. In addition, third branching tube (13) is connected to the upper side of cylindrical part (15) as shown in the figure, and third branching flow channel (13b) of third branching flow channel (13a) is opened to the upper side shown in the figure. Also, in this embodiment, third branching flow channel (13a) corresponds to the flow channel space in the present invention, and first branching tube (11) and second branching tube (12) correspond to the connecting ports in the present invention.

Said first branching tube (11), second branching tube (12) and third branching tube (13) are connected to cylindrical part (15) with a spacing of about 90° between them. Said first branching tube (11) and second branching tube (12) are set facing each other with cylindrical part (15) sandwiched between them. Also, third branching tube (13) is set at a spacing of 90° from said first branching tube (11) and second branching tube (12), respectively in the circumferential direction of cylindrical part (15). Said third branching flow channel (13a) is formed orthogonal to first branching flow channel (11a) and second branching flow channel (12a).

As shown in FIG. 4, third branching tube (13) is formed extending in the vertical direction from the periphery of cylindrical part (15), and it is composed of tapered portion (13c) having a tapered inner wall with the inner diameter becoming smaller as the location goes away from cylindrical part (15), and cylindrical portion (13d) formed extending from the tip of said tapered portion (13c) upward. Said tapered portion (13c) has third branching flow channel (13a) formed inside it, and, at the same time, it has step (13e) formed on its outer surface. Also, third branching flow channel (13a) formed inside tapered portion (13c) can be connected to said grooves (21), (22), so that the liquid in grooves (21), (22) can flow via said third branching flow channel (13a).

As shown in the figure, partition wall (13f) is set in third branching flow channel (13a). This partition wall (13f) is formed at a position in the same axial direction as that of partition wall (23) formed between two grooves (21), (22) formed on the outer periphery of valve body (20). In the state shown in FIG. 4, it is set between grooves (21), (22). Consequently, the liquid in said two grooves (21), (22) cannot go over said partition wall (13f) and cannot directly flow into each other.

Opening portion (13b) of third branching flow channel (13a) is opened on the upper side shown in the figure of cylindrical portion (13d) of third branching tube (13). Valve member (40) is mounted on this opening portion (13b). Said valve member (40) is composed of main body part (41), first supporting arm (42a) and second supporting arm (42b). They are formed integrally from a rubber like material. Said main body portion (41) is inserted in opening portion (13b), and said opening portion (13b) is blocked liquid tight. Said main body portion (41) is formed in a cylindrical shape. In the state shown in the figure, its outer contour is composed of outer surface (41a) as an end surface that faces to the outside, inner surface (41b) as an end surface that faces third branching flow channel (13a), and side peripheral surface (41c) as the peripheral surface between outer surface (41a) and inner surface (41b). Also, opening portion (13b) of third branching flow channel (13a) corresponds to the opening portion in the present invention.

Said main body portion (41) has its side peripheral surface (41c) in contact with the inner wall of cylindrical portion (13d) of third branching tube (13), and it is fitted into opening portion (13b) by the elastic force. Then, by pressing outer surface (41a) from the outside, it is possible to press it into the side of third branching flow channel (13a) as it is mounted in opening portion (13b).

As shown in the figure, inner slit (41d) is formed on main body portion (41). This inner slit (41d) is opened as a cut on inner surface (41b), and, at the same time, it is formed extending in a nearly vertical direction from the opening portion toward the side of outer surface (41a). Here, inner slit (41d) does not reach outer surface (41a), and it is not formed from inner surface (41b) through to outer surface (41a).

Figure 6:
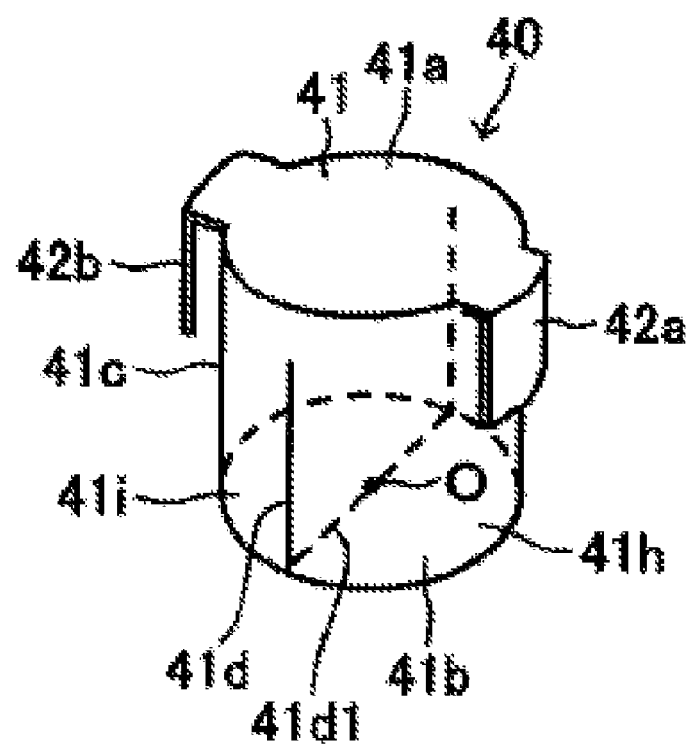
FIG. 6 is a schematic oblique view illustrating the valve member in Embodiment 1 of the present invention.

FIG. 6 is an oblique view schematically illustrating valve member (40) in this embodiment. As shown in FIG. 6, opening portion (41d1) on inner surface (41b) of inner slit (41d) is formed a linear opening portion (cut) that runs from the edge of the outer periphery of inner surface (41b) through center O to the edge on the opposite side. Consequently, by means of inner slit (41d), inner surface (41b) is bisected. Also, main body portion (41) is divided by said inner slit (41d) to first portion (41h) and second portion (41i). However, said first portion (41h) and second portion (41i) are not fully separated from each other. They may be formed as a common member in the upper portion of main body portion (41) as shown in the figure.

As shown in FIG. 1, first supporting arm (42a) and second supporting arm (42b) are formed extending outward from the opening edge portion of outer surface (41a) of main body portion (41) in the radial direction. In this embodiment, said supporting arms are attached at opposite positions on outer surface (41a), respectively. Also, as shown in FIG. 4, first supporting arm (42a) and second supporting arm (42b) are attached to the positions in the circumferential direction in plane symmetry with the plane having inner slit (41d) formed on it taken as the symmetrical plane of main body (41). Said supporting arms (42a), (42b) go over the upper end of cylindrical portion (13d) of third branching tube (13) as shown in the figure, and they reach around the outer wall side of cylindrical portion (13d) and tapered portion (13c).

As shown in FIG. 4, cover (51) made of a plastic material is attached to the outer periphery of tapered portion (13c) of third branching tube (13). This cover (51) is formed in a dome shape. Also, cover (51) has a round opening formed at its center. From this opening, cylindrical portion (13d) of third branching tube (13) is inserted, and it is mounted on third branching tube (13). Then, third branching tube (13) is attached to cover the entire circumference of tapered portion (13c). On the inner periphery of the lower end side of cover (51) as shown in the figure, groove (51a) is formed along the circumferential direction. As said groove (51a) is engaged to protruding strip (13g) formed in the circumferential direction on the lower outer periphery of tapered portion (13c), cover (51) is fixed on tapered portion (13c).

As shown in FIG. 4, protrusion (51b) is formed on the upper portion on the inner periphery of said cover (51). This protrusion (51b) is engaged to step (13e) formed on the outer periphery of tapered portion (13c). Said first supporting arm (42a) and second supporting arm (42b) are held in the portion where said protrusion (51b) is engaged to step (13e). Consequently, first supporting arm (42a) and second supporting arm (42b) are held and fixed between cover (51) and tapered portion (13c). By means of said supporting arms (42a), (42b) fixed in this way, main body portion (41) is supported as it hangs by first supporting arm (42a) and second supporting arm (42b).

In 3-way valve (100) of the present embodiment with the aforementioned constitution, holding portion (30) is rotated so that first branching flow channel (11a) is connected to groove (21) formed on valve body (20), and second branching flow channel (12a) is connected to groove (22). A medicine tube is attached to first branching tube (11) and second branching tube (12). A medicine solution flows from a medicine solution tube connected to first branching tube (11). Then said medicine solution flows from first branching flow channel (11a) to groove (21) of valve body (20). The medicine solution in groove (21) goes over partition wall (21c) into third branching flow channel (13a). Then, the medicine solution goes over partition wall (13f) in third branching flow channel (13a) into groove (22). It then flows from groove (22) into second branching flow channel (12a). In this way, a principal flow channel is formed.

Here, as shown in FIG. 4, opening portion (13b) of third branching tube (13) is blocked liquid tight by main body portion (41) of valve member (40), and it is in the closed state. Consequently, as explained above, the flow of the principal flow channel as aforementioned does not leak from third branching tube (13). Also, no impurity from the outside can go through opening portion (13b) of third branching tube (13) into third branching flow channel (13a).

Figure 7A:
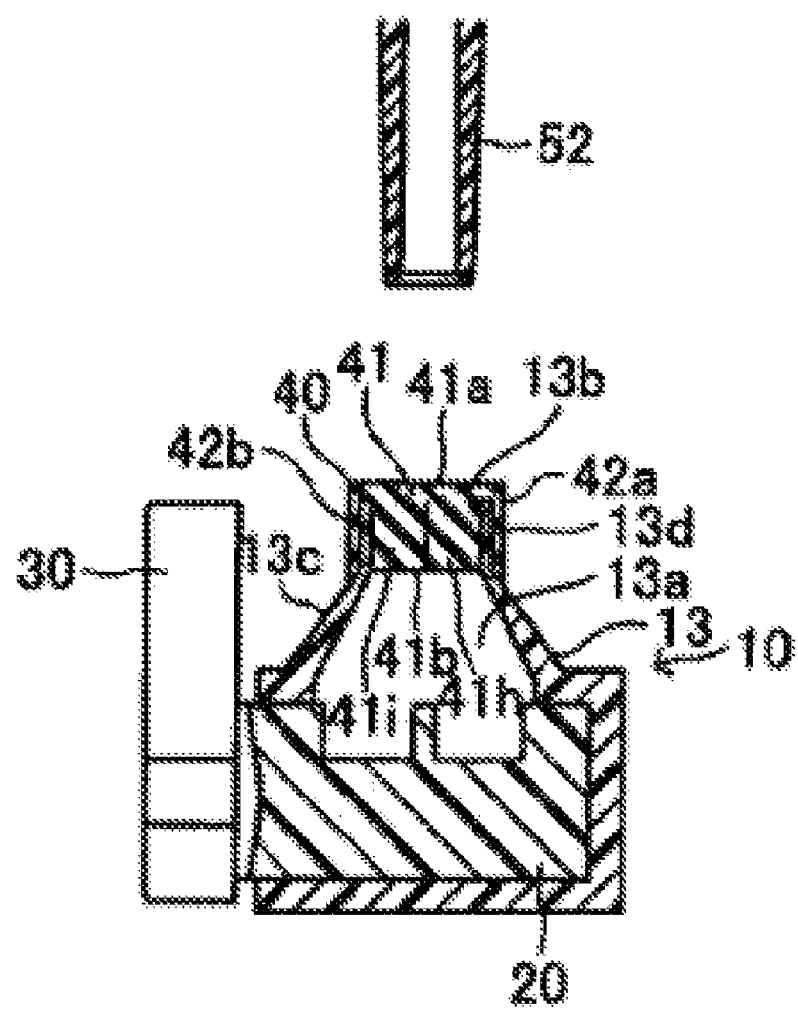
FIG. 7(a) is a perspective of the Luer syringe portion before insertion in the valve member of the third branching tube of the 3-way valve in Embodiment 1 in a mixing injection operation.
Figure 7B:
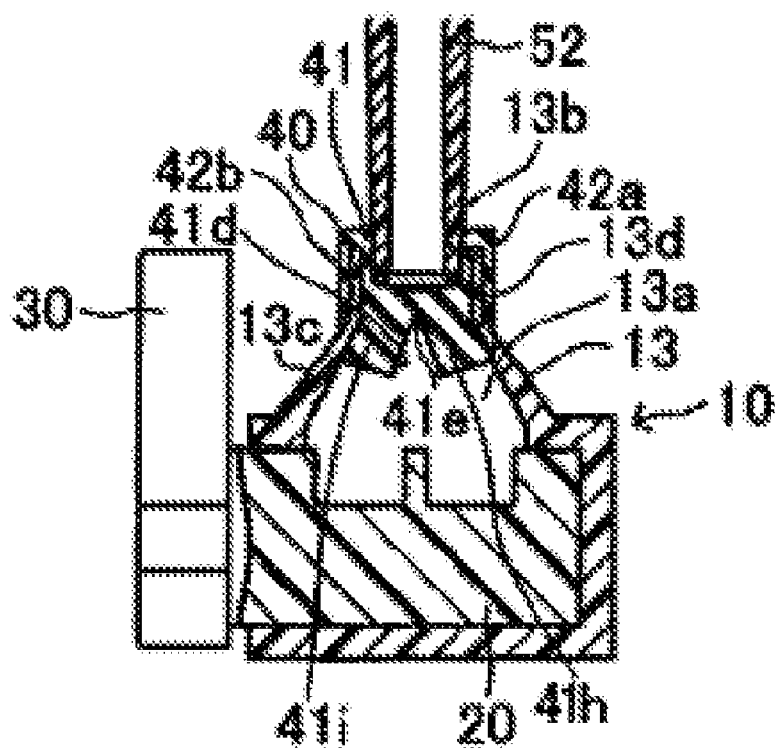
FIG. 7(b) is similar to FIG. 7(a) with the Luer syringe portion inserted into the valve member yet the valve member is still closed in the mixing injection operation.
Figure 7C:
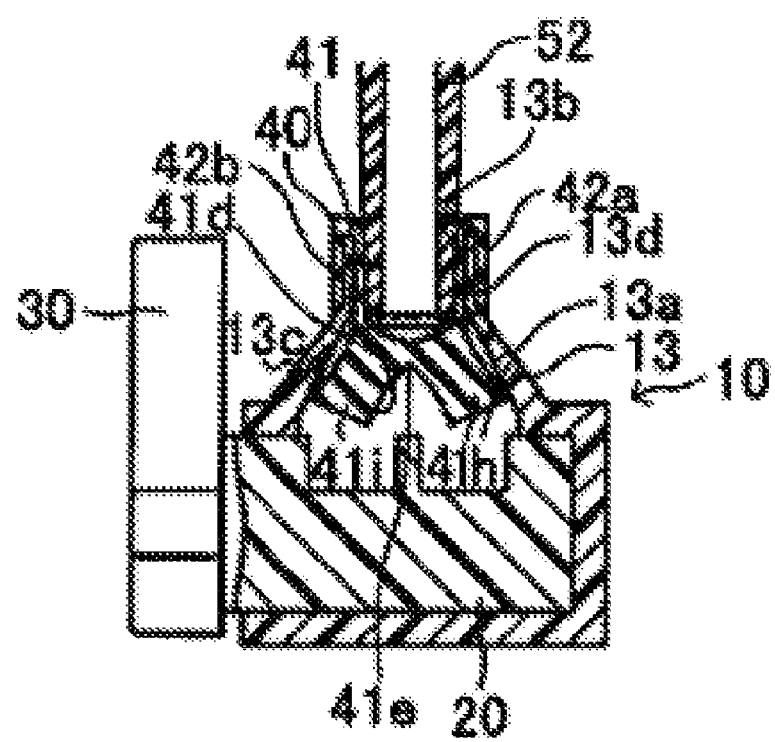
FIG. 7(c) is a perspective similar to FIG. 7(b) with the Luer syringe portion inserted in the valve member and the valve member being opened in the mixing injection operation.
Figure 8A:
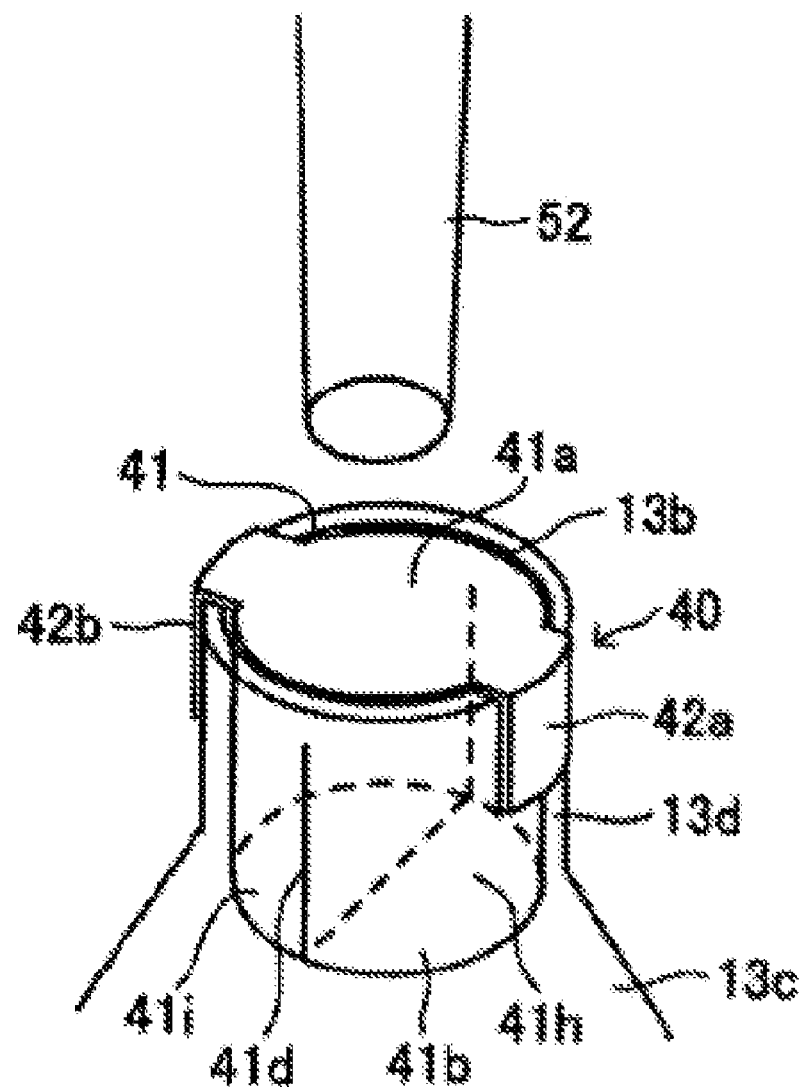
FIG. 8 is a schematic oblique view illustrating the same operation as that in FIGS. 7(a)-7(c)
Figure 8B:
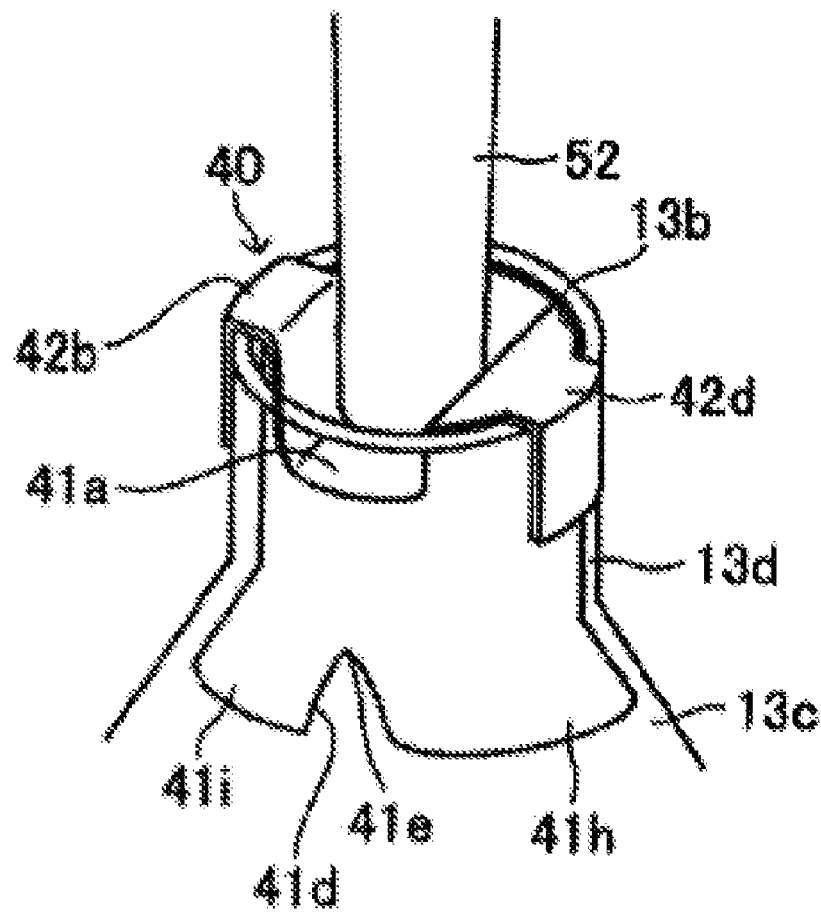
Figure 8C:
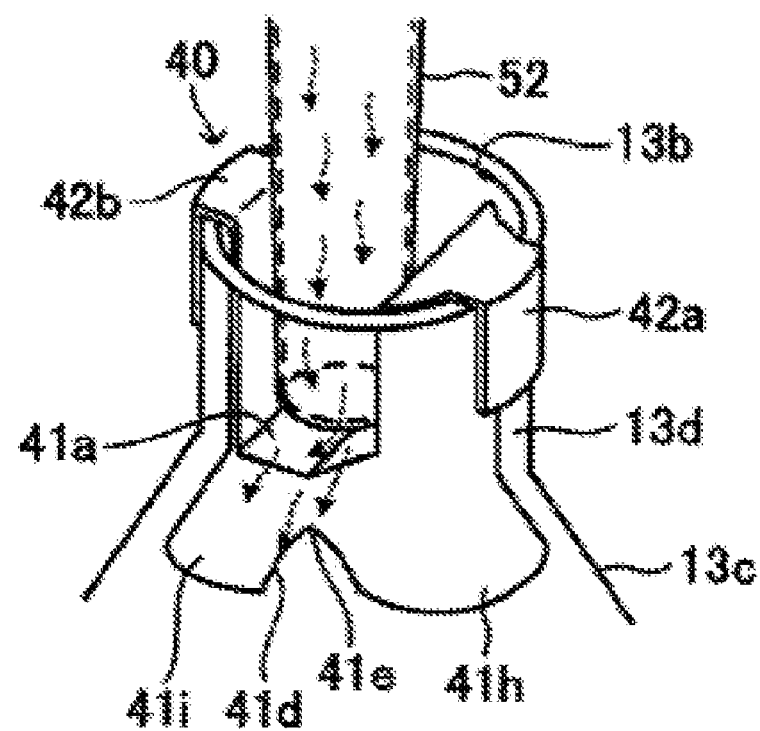

When a medicine solution is to be mixed and injected from the side of third branching tube (13) into the principal flow channel, the Luer syringe portion is inserted into main body portion (41) of valve member (40) so that the valve member is opened. FIGS. 7(a) (c) are schematic diagrams illustrating the operation in which said Luer syringe portion (52) is mounted in valve member (40) attached in opening portion (13b) of third branching tube (13), and the medicine solution from the syringe is fed into the principal flow channel. FIGS. 8(a) (c) are oblique views illustrating the state shown in FIGS. 7(a) (c). FIGS. 7(a) and 8(a) show the state before insertion of Luer syringe portion (52) into valve member (40). FIGS. 7(b) and 8(b) show the state when Luer syringe portion (52) is being inserted in valve member (40), while valve member (40) is still in the closed state. FIGS. 7(c) and 8(c) show the state in which Luer syringe portion (52) has been inserted, and valve member (40) is opened.

First of all, as shown in FIGS. 7(a) and 8(a), the tip of Luer syringe portion (52) of the syringe for filling the liquid to be mixed and injected is brought near valve member (40) attached to opening portion (13b) of third branching tube (13). Then, as shown in FIGS. 7(b) and 8(b), the tip portion of Luer syringe portion (52) is pressed on outer surface (41a) of main body portion (41) of valve member (40), and its outer surface (41a) is pressed to the side of third branching flow channel (13a) positioned on the lower side as shown in the figure. As a result, due to the pressing force of Luer syringe portion (52), main body portion (41) is pressed downward as shown in the figure and at the same time first supporting arm (42a) and second supporting arm (42b) are pulled and stretched.

Figure 9:
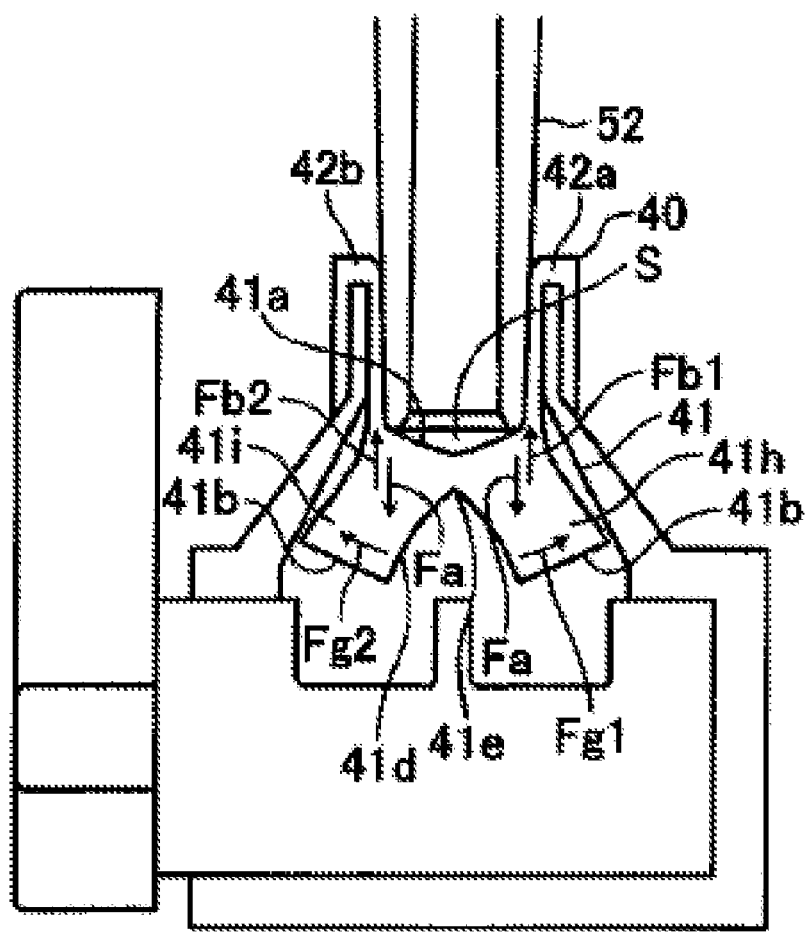
FIG. 9 is a diagram illustrating the relationship between the pressing force acting on the main body portion of the valve member and the pulling up force in Embodiment 1 of the present invention.

As first supporting arm (42a) and second supporting arm (42b) are pulled and stretched, the elastic force from said supporting arms (42a), (42b) acts on main body portion (41), and supporting arms (42a), (42b) generate a force for pulling up main body portion (41) (pulling up force) in order to return main body portion (41) to the original position. FIG. 9 is a diagram illustrating the relationship between the pressing force from Luer syringe portion (52) and the pulling up force from first supporting arm (42a) and second supporting arm (42b). As shown in FIG. 9, pressing force Fa acting by the tip opening portion of Luer syringe portion (52) on main body portion (41) of valve member (40) operates main body portion (41) in the pressing in direction (downward direction as shown in the figure) on the side of third branching flow channel (13a). On the other hand, pulling up force Fb1 applied by first supporting arm (42a) on main body portion (41) acts in the direction to pull up main body portion (41) from the side of third branching flow channel (13a) to the outside (the upward direction shown in the figure). Similarly, pulling up force Fb2 applied by second supporting arm (42b) on main body portion (41) also acts in the direction to pull up main body portion (41) from the side of third branching flow channel (13a) to the outside (upward direction as shown in the figure). Because pressing force Fa and pulling up forces Fb1, Fb2 act at different positions in opposite directions, a pair of forces act on main body portion (41).

The pair of forces act between pressing force Fa and pulling up force Fb1, and between pressing force Fa and pulling up force Fb2, respectively. Also, the line of action of pulling up forces Fb1 and Fb2 is positioned on the outer side in the radial direction of main body portion (41) with respect to the line of action of pressing force Fa. Consequently, for main body portion (41), the portion near its central portion is pressed to the side of third branching flow channel (13a), and the portion near its outer peripheral edge is pulled up by supporting arms (42a), (42b). In this state, the side of outer surface (41a) of main body portion (41) is acted on by a force that bends it inward, while the side of inner surface (41b) of main body portion (41) is acted by a force that pulls it from the center toward the outer periphery as indicated by arrows Fg1 and Fg2 in the figure.

Also, inner slit (41d) is formed on main body portion (41), and said inner slit (41d) is formed to bisect inner surface (41b). The plane where said inner slit (41d) is formed becomes the symmetrical plane between the portion where first supporting arm (42a) is attached to main body portion (41) and the portion where second supporting arm (42b) is attached to main body portion (41), and, as far as first portion (41h) and second portion (41i) divided by inner slit (41d) are concerned, said first portion (41h) is supported by outer surface (41a), and said second portion (41i) is supported by second supporting arm (42b). Consequently, the force indicated by arrow Fg1 mainly acts on first portion (41h), and the force indicated by arrow Fg2 mainly acts on second portion (41i). As a result, as shown in FIGS. 7(c), 8(c) and 9, inner slit (41d) is opened, and said first portion (41h) and second portion (41i) divided by said inner slit (41d) are separated from each other in the lower portion shown in the figure.

In said constitution, when inner slit (41d) is opened, as can be seen from FIG. 9, root portion (41e) of inner slit (41d) is pressed down as shown in the figure. Then, as it is pulled and diverges, outer surface (41a) of main body portion (41) is also pressed downward as shown in the figure, so that recess S is formed near the center. Said recess S is formed along inner slit (41d) as a groove from the edge portion of the outer periphery of outer surface (41a) to the edge portion on the opposite side. Said recess S is formed between the tip opening portion of Luer syringe portion (52) and the outer surface of main body portion (41). Consequently, when Luer syringe portion (52) presses outer surface (41a) of main body portion (41) to about the same height as the upper end portion of tapered portion (13c) (the portion connected to cylindrical portion (13d)), said recess S becomes connected to the interior of third branching flow channel (13a). Then, the medicine solution is fed from Luer syringe portion (52) to said groove shaped recess S, and it then flows from recess S to third branching flow channel (13a). In this way, mixing injection is performed from third branching flow channel (13a). Here, the portion of outer surface (41a) where recess S is formed corresponds to the connecting surface in the present invention.

When Luer syringe portion (52) is pulled out of the state in which recess S is connected to third branching flow channel (13a), pressing force Fa from Luer syringe portion (52) is eliminated. Consequently, forces Fg1, Fg2 also do not work, and inner slit (41d) is closed. At the same time, only pulling up forces Fb1, Fb2 act from supporting arms (42a), (42b) on main body portion (41). Consequently, main body portion (41) is pulled up by said two supporting arms (42a), (42b), and, as shown in FIGS. 7(a) and 8(a), it returns to the base position. In this state, outer surface (41a) of main body portion (41) is not connected to third branching flow channel (13a). Also, because opening portion (13b) of third branching tube (13) is blocked liquid tight, for main body portion (41), the connection between third branching flow channel (13a) to the outside is cut off.

As explained above, 3-way valve (100) has the following constitution in the present embodiment: valve member (40) attached to opening portion (13b) of third branching tube (13) that forms housing (10) has main body portion (41) as well as first supporting arm (42a) and second supporting arm (42b) as the supporting portion, and, when main body portion (41) is pressed by the Luer syringe portion into third branching flow channel (13a), outer surface (41a) of main body portion (41) becomes connected to third branching flow channel (13a). Consequently, by pressing outer surface (41a) of main body portion (41) from the outside by the Luer syringe portion, together with main body portion (41), the Luer syringe portion is pressed into third branching flow channel (13a), and it is connected to third branching flow channel (13a). When the liquid to be fed is loaded from the Luer syringe portion in this state, the loaded fluid flows from outer surface (41a) to third branching flow channel (13a). In this way, feeding of the liquid is performed.

Also, when the Luer syringe portion is lifted from outer surface (41a) of main body portion (41) and the pressing force is released, main body portion (41) recovers the original state (the state in which it is not pressed in third branching flow channel (13a)) under the pulling up force (elastic force) applied by first supporting arm (42a) and second supporting arm (42b). In the original state, main body portion (41) has opening portion (13b) of third branching tube (13) blocked liquid tight. Consequently, connection of third branching flow channel (13a) to the outside is cut off. In this way, for 3-way valve (100) in the present embodiment, as main body portion (41) is pressed into the flow channel space by the pressing force from the outside (pressure), outer surface (41a) of main body portion (41) itself is connected to the flow channel space. This system is different from the conventional system in which connection is made between the outside and the flow channel space through a slit formed through the valve member. Consequently, there is no need to have a through slit formed on the valve member as would be needed in the prior art. As a result, for the 3-way valve obtained, it is possible to prevent the half open state of the valve member due to degradation of the slit, to ensure a cutoff of the connection to the outside when not in use with high reliability, and to have little chance of leakage or bacterial reproduction.

In addition, in the present embodiment, for valve member (40), main body portion (41) and the supporting part (first supporting arm (42a) and second supporting arm (42b)) are integrally formed from a rubber material. Consequently, valve member (40) can be easily formed.

In addition, main body portion (41) of valve member (40) in the present embodiment is formed in the shape of a cylindrical rubber valve having outer surface (41a) and inner surface (41b) as the end surfaces. With said shape, side peripheral surface (41c) can make contact with the inner peripheral surface in a wide range of cylindrical portion (13d) connected to opening portion (13b) of third branching tube (13), and it is possible to guarantee sufficient liquid tightness of third branching flow channel (13a).

In the present embodiment, for main body portion (41), while there is opening portion (41d1) opened on inner surface (41b), inner slit (41d) extending in the direction from inner surface (41b) toward outer surface (41a) is formed. Said inner slit (41d) is opened by the pair of forces consisting of the pressing force of the Luer syringe portion and the pulling up forces from first supporting arm (42a) and second supporting arm (42b). Due to opening of said inner slit (41d), recess S is formed on outer surface (41a) at the portion corresponding to inner slit (41d). Because said recess S is formed between the tip of the Luer syringe portion and outer surface (41a), the liquid to be mixed and injected from the Luer syringe portion can flow from recess S to third branching flow channel (13a) with a high reliability.

In the present embodiment, first supporting arm (42a) and second supporting arm (42b) are symmetrically attached with respect to main body portion (41). Consequently, the pulling up forces generated by the two supporting portions act uniformly on main body portion (41). As a result, a good balance is realized between the pressing force and the pulling up force. Hence, it is possible to prevent the problem of inclination when the main body portion is pressed due to losing said balance.

Also, in the present embodiment, inner slit (41d) is formed to bisect inner surface (41b) of main body portion (41). When formed in this way, inner slit (41d) is opened by the pair of forces. Also, when inner slit (41d) is opened, recess S formed on outer surface (41a) becomes a groove along opening portion (41d1) on inner surface (41b) of inner slit (41d). Consequently, a portion of the groove shaped recess acts as a flow channel, and the liquid to be fed can flow along the groove shaped recess to third branching flow channel (13a). In this way, because the liquid to be fed flows along the groove shaped recess, no liquid spills out of the outer surface, and the liquid can be fed at an even higher efficiency.

In the following, an explanation will be given regarding Embodiment 2 of the present invention. This embodiment has the characteristic feature that an outer surface is set on the main body portion of the valve member. The other characteristic features are the same as those in said Embodiment 1. In the embodiment to be explained below, the same part numbers as those adopted in the above will be adopted, and they will not be explained again. An explanation will be given only for the features that are different from the aforementioned embodiment.

Figure 10:
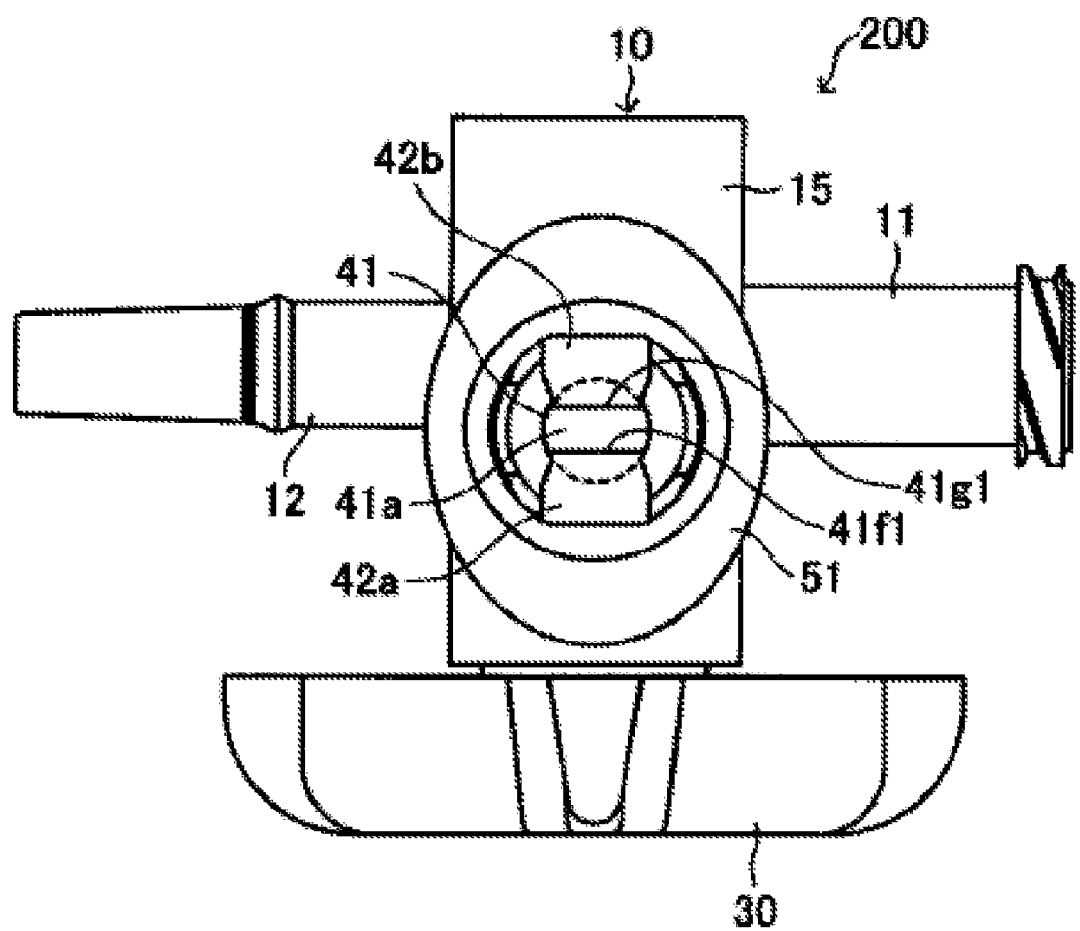
FIG. 10 is a plan view of the 3-way valve in Embodiment 2.
Figure 11:
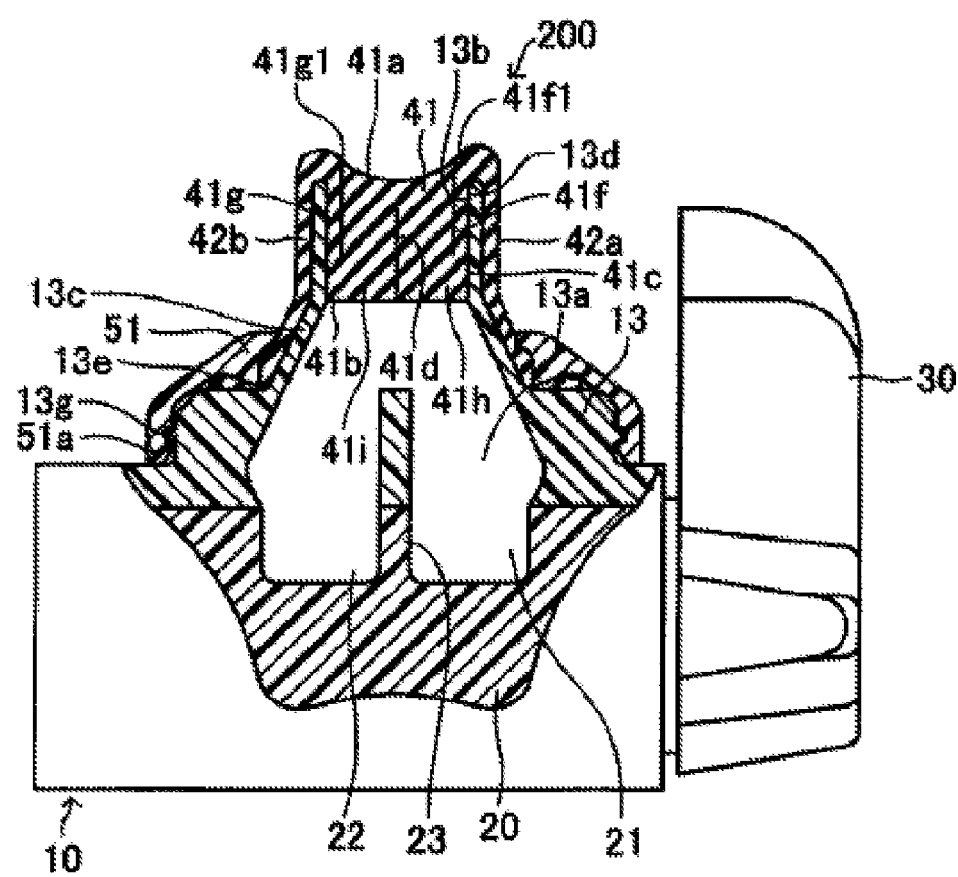
FIG. 11 is a partial cross sectional view illustrating the 3-way valve in Embodiment 2 of the present invention.

FIG. 10 is a plan view of the 3-way valve in this embodiment. FIG. 11 is a cross sectional view of the side surface portion. FIG. 11 corresponds to FIG. 4 in Embodiment 1. As can be seen from the figure, for 3-way valve (200) in the present embodiment, on main body portion (41) of valve member (40), first outer slit (41f) and second outer slit (41g) are formed. For said first outer slit (41f), among outer surface (41a) of main body portion (41), there is opening portion (41f1) opening near where first supporting arm (42a) is attached, and it is formed hanging from said opening portion (41f1) toward the side of inner surface (41b). For second outer slit (41g), among outer surface (41a), there is opening portion (41g1) opening near where second supporting arm (42b) is mounted, and it is formed hanging from said opening portion (41g1) toward the side of inner surface (41b). Here, first outer slit (41f) and second outer slit (41g) do not reach inner surface (41b), and they are not formed from outer surface (41a) through to reach inner surface (41b).

As can be seen from FIG. 10, opening portion (41f1) of first outer slit (41f) which is formed on the outer surface of main body portion (41) and opening portion (41g1) of second outer slit (41g) are formed from an edge portion through to the other edge portion on outer surface (41a) so as to divide outer surface (41a). Consequently, outer surface (41a) of main body portion (41) is divided into three portions by opening portion (41*f*1) of first outer slit (41*f*) and opening portion (41*g*1) of second outer slit (41*g*). Also, opening portion (41*f*1) and opening portion (41*g*1) are formed parallel to each other.

In addition, as shown in FIG. 11, first outer slit (41*f*) and second outer slit (41*g*) are formed parallel to inner slit (41*d*) that opens on inner surface (41*b*) of main body portion (41). Also, in this embodiment, first outer slit (41*f*) and second outer slit (41*g*) are formed on main body portion (41) so that they become symmetric with the plane where inner slit (41*d*) is formed as the symmetrical plane. The characteristic features other than the constitution of said first outer slit (41*f*) and second outer slit (41*g*) are the same as those in said Embodiment 1. Consequently, the same part numbers are adopted, and they will not be explained again.

Figure 12A:
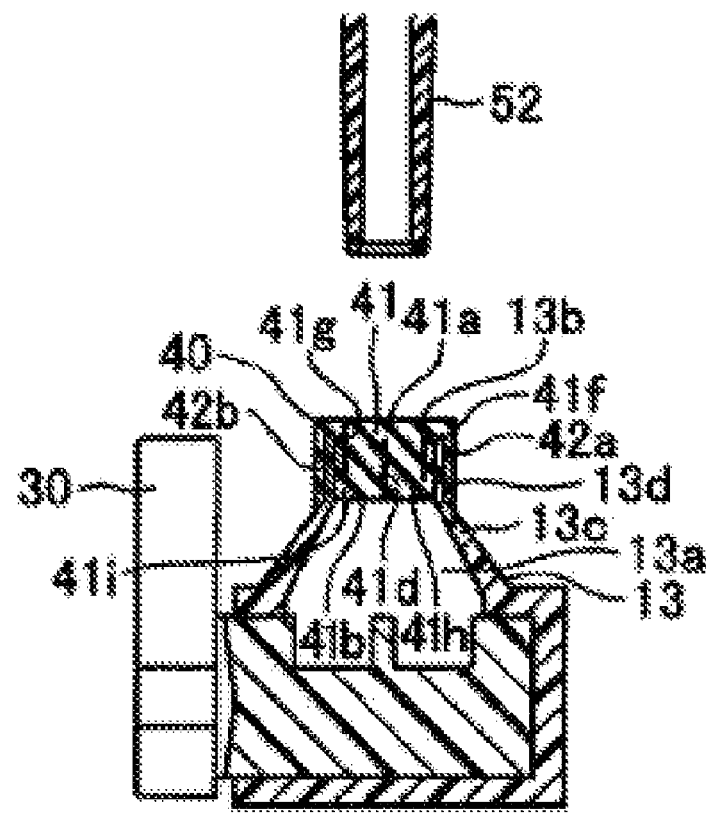
FIG. 12(a) is a perspective of the Luer syringe portion before insertion in the valve member of the third branching tube of the 3-way valve in Embodiment 2 in a mixing injection operation.
Figure 12B:
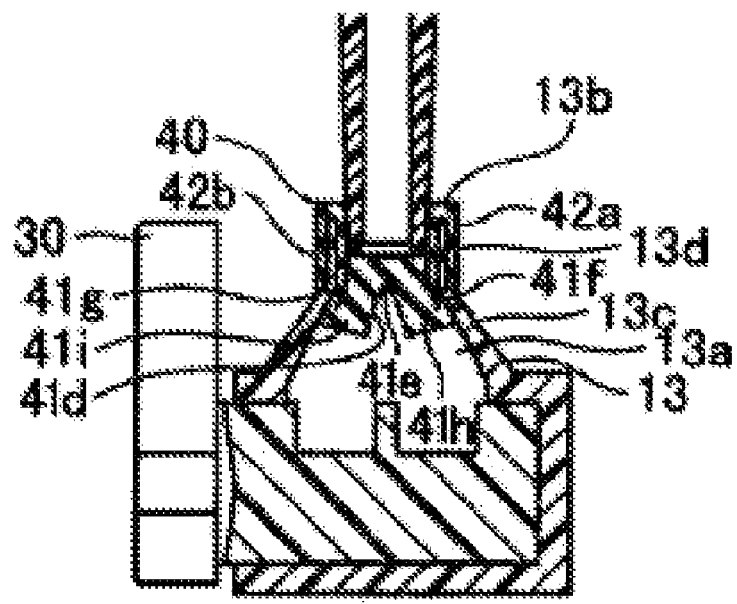
FIG. 12(b) is similar to FIG. 12(a) with the Luer syringe portion inserted into the valve member yet the valve member is still closed in the mixing injection operation.

In the following, an explanation will be given regarding 3-way valve (200) with said constitution in the case when the medicine solution is mixed and injected from third branching tube (13). FIGS. 12(*a*) (*c*) are schematic diagrams illustrating the operation of feeding of the medicine solution from a syringe as Luer syringe portion (52) of the syringe is attached to valve member (40) mounted on opening portion (13*b*) of third branching tube (13). FIGS. 13(*a*) (*c*) are oblique views illustrating the state shown in FIGS. 11(*a*) (*c*). FIGS. 12(*a*) and 13(*a*) show the state before insertion of Luer syringe portion (52) into valve member (40). FIGS. 12(*b*) and 13(*b*) show the state in which Luer syringe portion (52) is inserted in valve member (40), yet valve member (40) is still closed. FIGS. 12(*c*) and 13(*c*) show the state in which Luer syringe portion (52) has been inserted into valve member (40), and valve member (40) is opened.

First of all, as shown in FIGS. 12(*a*) and 13(*a*), the tip of Luer syringe portion (52) of the syringe filled with the liquid to be mixed and injected is brought near valve member (40) attached to opening portion (13*b*) of third branching tube (13). Then, as shown in FIGS. 12(*b*) and 13(*b*), the tip portion of Luer syringe portion (52) is pressed on outer surface (41*a*) of main body portion (41) valve member (40), and said outer surface (41*a*) is pressed to the side of third branching flow channel (13*a*) located on the lower side as shown in the figure. Here, in the present embodiment, main body portion (41) of valve member (40), first supporting arm (42*a*) and second supporting arm (42*b*) are formed integrally from a rubber like substance. Consequently, due to the pressing force of Luer syringe portion (52), while main body portion (41) is pressed down as shown in the figure, first supporting arm (42*a*) and second supporting arm (42*b*) are pulled and stretched.

When first supporting arm (42*a*) and second supporting arm (42*b*) are pulled and as they are stretched the elastic forces from said supporting arms (42*a*), (42*b*) act on main body portion (41), and supporting arms (42*a*), (42*b*), generating a force for pulling up main body portion (41) (pulling up force) so as to reset main body portion (41) to the original position. In this case, as explained in Embodiment 1, a pair of forces act on main body portion (41), the pressing force and pulling up force. Due to the pair of forces, as shown in the figure, inner slit (41*d*) is opened, and first portion (41*h*) and second portion (41*i*) divided by inner slit (41*d*) are separated from each other in the lower portion shown in the figure.

As inner slit (41*d*) is opened, root portion (41*e*) of inner slit (41*d*) is pressed down as shown in the figure. As a result, outer surface (41*a*) of main body portion (41) is also pulled down, and, as shown in FIGS. 12(*c*) and 13(*c*), recess S if formed near the center. Said recess S is formed as a groove along inner slit (41*d*) to the edge of outer surface (41*a*). Also, said recess S is formed between the tip opening portion of Luer syringe portion (52) and the outer surface of main body portion (41). Consequently, as Luer syringe portion (52) is used to press outer surface (41*a*) of main body portion (41) to the same height as that of the upper end portion of tapered portion (13*c*) (the portion connected to cylindrical portion (13*d*)), recess S becomes connected to the interior of third branching flow channel (13*a*). Then, the medicine solution is fed from Luer syringe portion (52) to said groove shaped recess S, and it then flows from recess S to third branching flow channel (13*a*). In this way, mixing and injection are performed from third branching flow channel (13*a*). Here, the portion of outer surface (41*a*) where recess S is formed corresponds to the connecting surface in the present invention.

Figure 14:
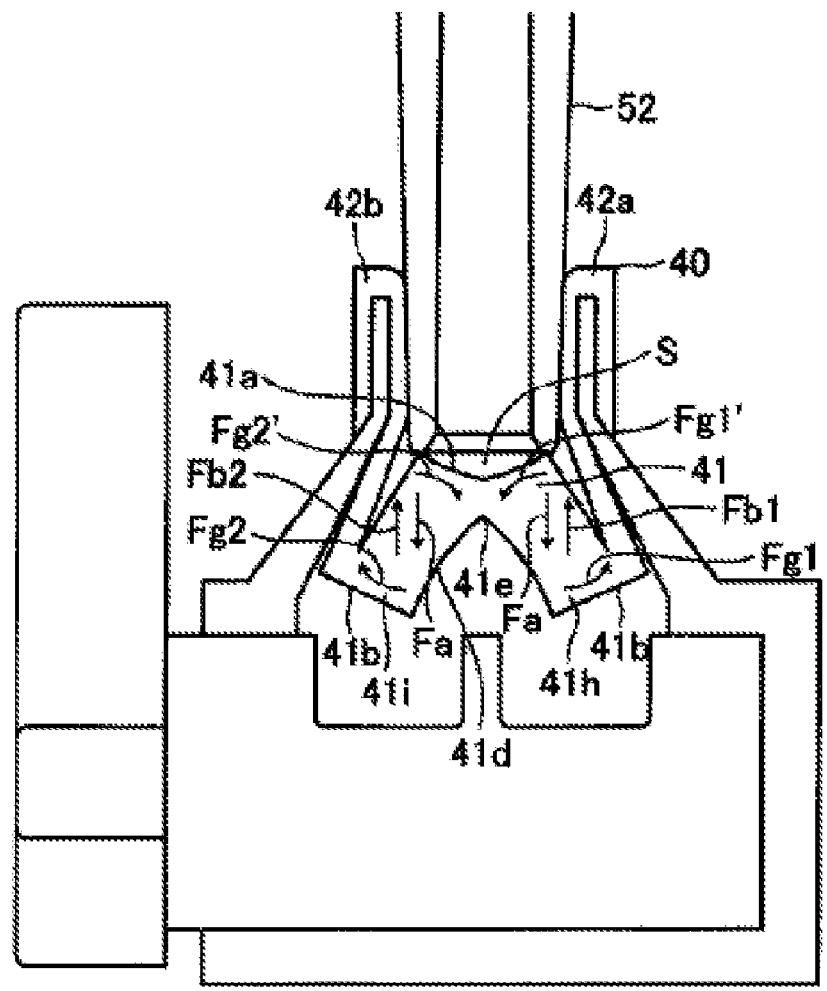
FIG. 14 is a diagram illustrating the relationship between the pressing force acting on the main body portion of the valve member and the pulling up force in Embodiment 2 of the present invention.

FIG. 14 is a diagram illustrating the relationship between the pressing force from Luer syringe portion (52) and the pulling up force applied by first supporting arm (42*a*) and second supporting arm (42*b*). As shown in FIG. 14, pressing force Fa applied by the tip opening portion of Luer syringe portion (52) on main body portion (41) of valve member (40) acts in the pressing direction (downward direction as shown in the figure) of main body portion (41) to the side of third branching flow channel (13*a*). On the other hand, pulling up force Fb1 applied from main body portion (41) of first supporting arm (42*a*) from third branching flow channel (13*a*) to the outside (upward direction as shown in the figure) acts in the pulling up direction on main body portion (41) from the side of third branching flow channel (13*a*) to the outside. Similarly, pulling up force Fb2 applied by second supporting arm (42*b*) on main body portion (41) also acts in the pull up direction on main body portion (41) from the side of third branching flow channel (13*a*) toward the outside (upward direction shown in the figure). Because pressing force Fa and pulling up forces Fb1, Fb2 act on different locations and in opposite directions, a pair of forces act on main body portion (41).

As explained with reference to said Embodiment 1, due to the pair of forces acting on main body portion (41), for main body portion (41), the portion near the central portion is pressed to the side of third branching flow channel (13*a*), and the portion near the outer peripheral edge is pulled up by supporting arms (42*a*), (42*b*). In this state, as indicated by arrows Fg1 and Fg2 in the figure, the side of inner surface (41*b*) of main body portion (41) is pulled by a force acting from the center toward the outer periphery. Consequently, inner slit (41*d*) is opened, and first portion (41*h*) and second portion (41*i*) divided by inner slit (41*d*) are separated from each other in the lower portion as shown in the figure.

On the other hand, on the side of outer surface (41*a*) of main body portion (41), as indicated by arrows Fg1' and Fg2' shown in the figure, forces act to bend it inward. In this case, because first supporting arm (42*a*) and second supporting arm (42*b*) shown in the figure are attached to the edge portion of outer surface (41*a*) of main body portion (41), for the portion near the base end portion of said supporting arms, forces act in the directions indicated by arrows Fg1' and Fg2', so that a stress applies.

At this point, in the present embodiment, first outer slit (41*f*) is formed near the portion where first supporting arm (42*a*) is attached, and second outer slit (41*g*) is formed near the portion where second supporting arm (42*b*) is attached. Consequently, by opening said slits (42*f*), (42*g*), forces act on these portions. Consequently, it is possible to relax the concentration of stress near them. As a result, in the present embodiment, the concentration of stress acting on outer surface (41*a*) of main body portion (41) can be relaxed, the reliability of the valve member rises, and this contributes to an increase in the service lifetime of the valve member.

Figure 12C:
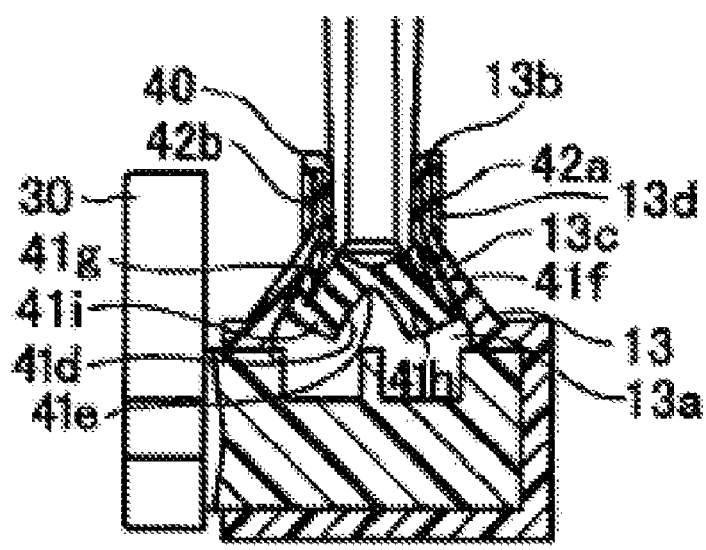
FIG. 12(c) is a perspective similar to FIG. 12(b) with the Luer syringe portion inserted in the valve member and the valve member being opened in the mixing injection operation.
Figure 13A:
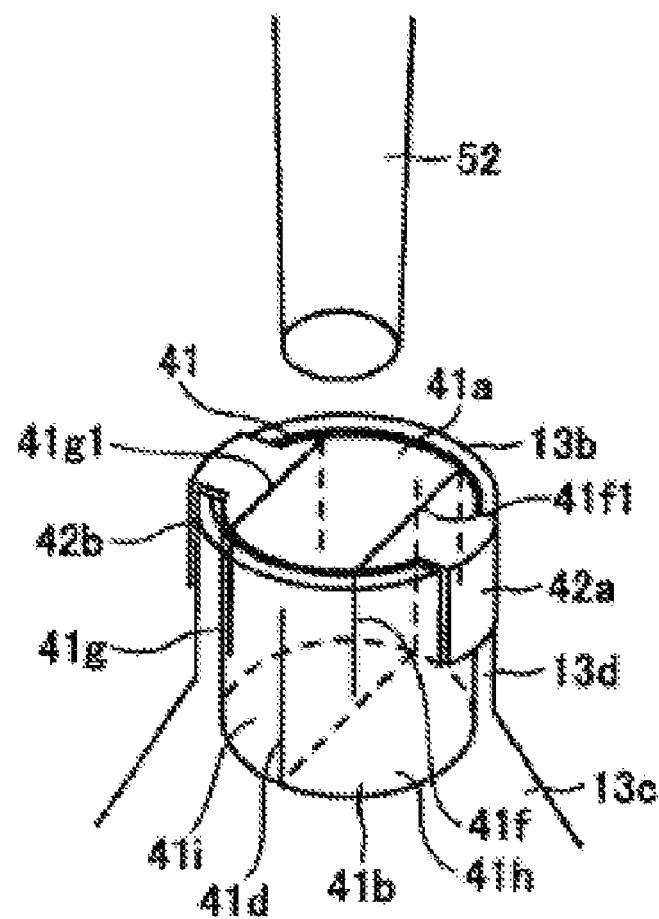
FIG. 13 is a schematic oblique view illustrating the same operation as that shown in FIGS. 12(a)-12(c)
Figure 13B:
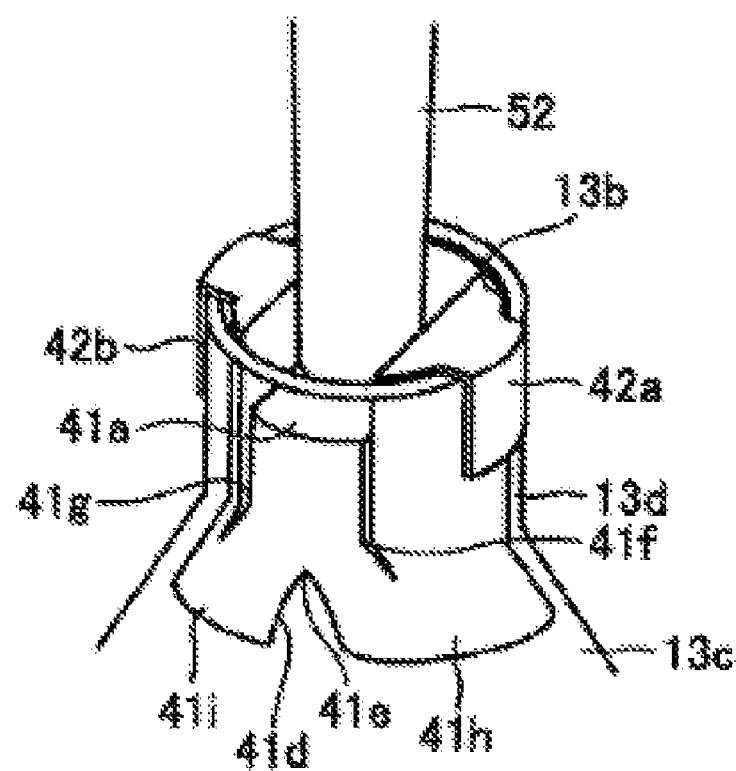
Figure 13C:
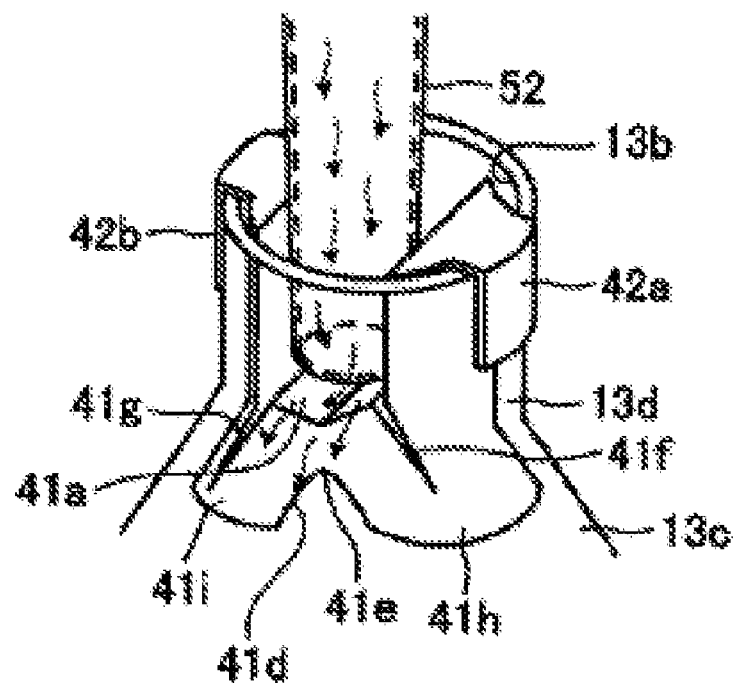

When Luer syringe portion (52) is pulled out of the state shown in FIGS. 12(c), 13(c) and 14, pressing force Fa from Luer syringe portion (52) is eliminated. Consequently, forces Fg1, Fg2, Fg1', Fg2' do not operate, and inner slit (41d), first outer slit (41f) and second outer slit (41g) are closed. At the same time, only pulling up forces Fb1, Fb2 from first supporting arm (42a) and second supporting arm (42b) act on main body portion (41). Consequently, main body portion (41) is pulled up by first supporting arm (42a) and second supporting arm (42b), and, as shown in FIGS. 12(a) and 13(a), it recovers to the original state. In this state, outer surface (41a) of main body portion (41) is not connected to third branching flow channel (13a). Also, because main body portion (41) is attached to opening portion (13b) of third branching tube (13) liquid tight, the connection between the third branching flow channel (13a) and the outside is cut off.

In the following, an explanation will be given regarding Embodiment 3 of the present invention. In this embodiment, the connector of the present invention is not a 3-way valve, and a mixing injector for mixing and injecting the liquid from halfway on the flow channel is adopted. Except for this characteristic feature, the other characteristic features are the same as those in said Embodiment 1.

Figure 15A:
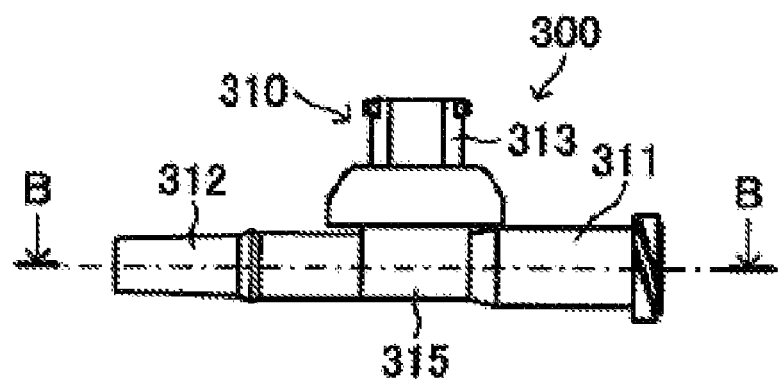
FIG. 15(a) is a front view of a mixing injector of Embodiment 3 of the present invention.
Figure 15B:
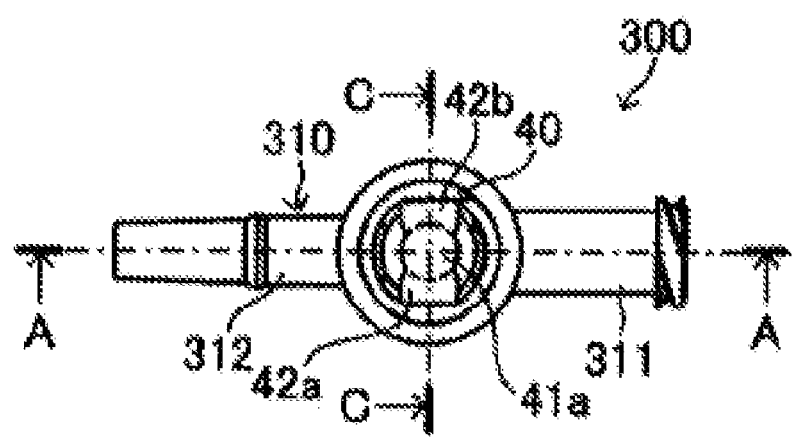
FIG. 15(b) is a plan view of the mixing injector of Embodiment 3.
Figure 15C:
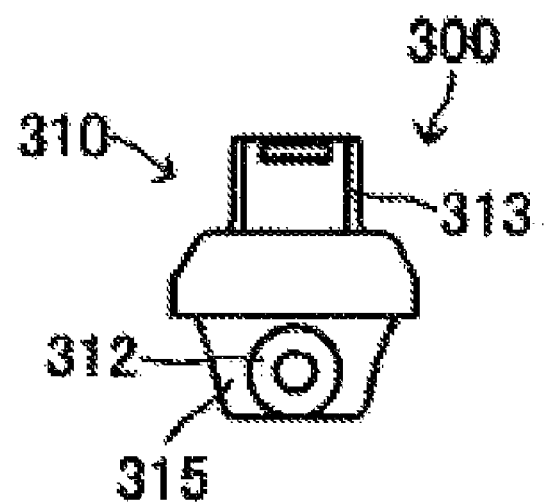
FIG. 15(c) is a side view of the mixing injector of Embodiment 3.
Figure 16A:
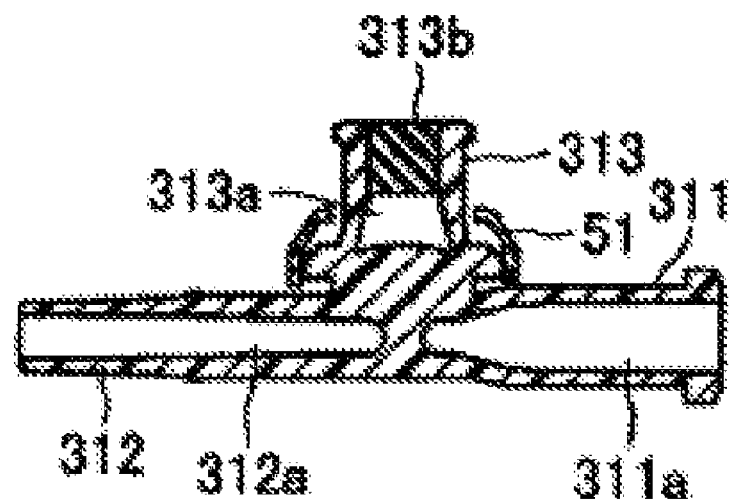
FIG. 16(a) is a cross sectional view of the mixing injector in Embodiment 3 taken across A-A of FIG. 15(b)
Figure 16B:
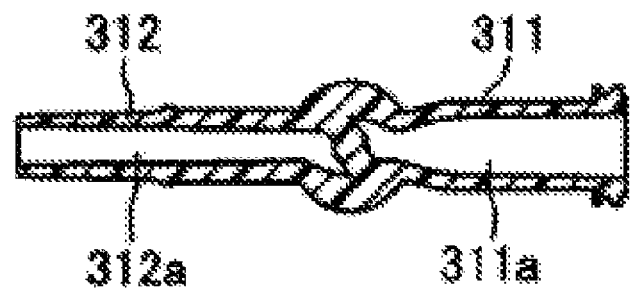
FIG. 16(b) is a cross sectional view of the mixing injector in Embodiment 3 taken across B-B of FIG. 15(a)
Figure 16C:
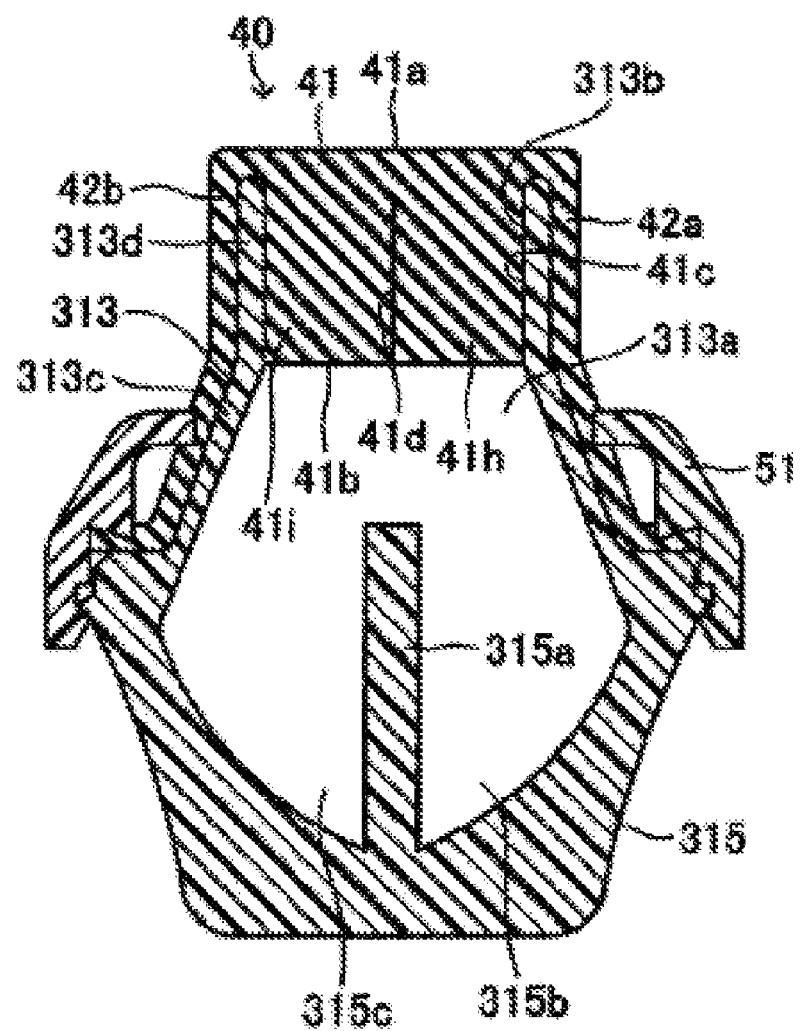
FIG. 16(c) is a cross sectional view of the mixing injector in Embodiment 3 taken across C-C of FIG. 15(b)

FIG. 15(a) is a front view illustrating the mixing injector in the present embodiment. FIG. 15(b) is its plan view, and FIG. 15(c) is its side view. FIG. 16(a) is a cross sectional view taken across A-A in FIG. 15(b). FIG. 16(b) is a cross sectional view taken across B-B of FIG. 15(a), and FIG. 16(c) is a cross sectional view taken across C-C of FIG. 15(b).

As can be seen from these figures, mixing injector (300) has housing (310). This housing (310) has first branching tube (311), second branching tube (312), third branching tube (313), and central merging portion (315). The various branching tubes are connected at central merging portion (315). In said branching tubes, respective branching flow channels are formed (first branching flow channel (311a), second branching flow channel (312a), and third branching flow channel (313a)). Also, as can be seen from FIG. 16(c), in central merging portion (315), partition wall (315a) is formed. By means of said partition wall (315a), the inner space of partition wall (315) is divided to first connecting space (315b) and second connecting space (315c). Here, first connecting space (315b) and second connecting space (315c) can be connected via third branching flow channel (313a) positioned in the upper portion of partition wall (315a) as shown in the figure.

Also, first connecting space (315b) is connected to first branching flow channel (311a), and second connecting space (315c) is connected to second branching flow channel (312a). Consequently, first branching flow channel (311a) is connected via first connecting space (315b) and second connecting space (315c) to second branching flow channel (312a).

As shown in FIGS. 15(a) and 16(a), first branching tube (311), second branching tube (312) and third branching tube (313) are connected to central merging part (315) with a spacing of about 90°. Said first branching tube (311) and second branching tube (312) are set facing each other. Also, third branching tube (313) is set spaced 90° from first branching tube (311) and second branching tube (312), respectively.

As shown in FIG. 16(c), third branching tube (313) is composed of tapered portion (313c) having a tapered inner wall, and cylindrical portion (313d) formed in a cylindrical shape extending upward from the tip of tapered portion (313c) as shown in the figure. Then, opening portion (313b) is formed at the tip of cylindrical portion (313d). Said tapered portion (313c) has third branching flow channel (313a) formed inside it. Said third branching flow channel (313a) is connected to both first connecting space (315b) and second connecting space (315c) in central merging part (315) located in the lower portion. In addition, the other features of the constitution, especially the features of valve member (40), are the same as those in said Embodiment 1, and the same part numbers are adopted here. They will not be explained again.

In mixing injector (300) of the present embodiment with the aforementioned constitution, the medicine solution flows from the medicine solution tube connected to first branching tube (311). Then, the medicine solution flows from first branching flow channel (311a) to first connecting space (315b) of central merging part (315). The medicine solution in first connecting space (315b) gets over partition wall (315a) into third branching flow channel (313a). Then, the medicine solution flows from the interior of third branching flow channel (313a) and enters second connecting space (315c) formed on the opposite side of first connecting space (315b) with partition wall (315a) sandwiched between them. Then, it flows from second connecting space (315c) to second branching flow channel (312a). In this way, the flow of the principal flow channel is formed.

Here, as shown in FIG. 16(c), opening portion (313b) of third branching tube (313) is blocked liquid tight by main body portion (41) of valve member (40). Consequently, as explained above, for the flow in the principal flow channel, there is no leak from third branching tube (313). Also, no impurity can enter from the outside via opening portion (313b) of third branching tube (313) to third branching flow channel (313a).

When no medicine solution is to be mixed and injected from the side of third branching tube (313), the Luer syringe portion of the syringe is inserted into main body portion (41) of valve member (40). Then, as the Luer syringe portion is used to press main body portion (41) of valve member (40) into third branching flow channel (313a), valve member (40) is opened. The principle of the operation pertaining to opening of valve member (40) and the connection of outer surface (41a) of main body portion (41) to third branching flow channel (313a) is the same as that in said Embodiment 1, and it will not be explained in detail again. In this way, the present invention also can be adopted in a mixing injector.

In the following, an explanation will be given regarding Embodiment 4 of the present invention. The present embodiment is characterized by the fact that the connector of the present invention is attached to the end portion of the flow channel, and, while the flow channel is usually closed, it is opened when a tube or the Luer syringe portion of syringe is attached so that it can be used as a connector. The remaining features are the same as those in Embodiment 1.

Figure 17A:
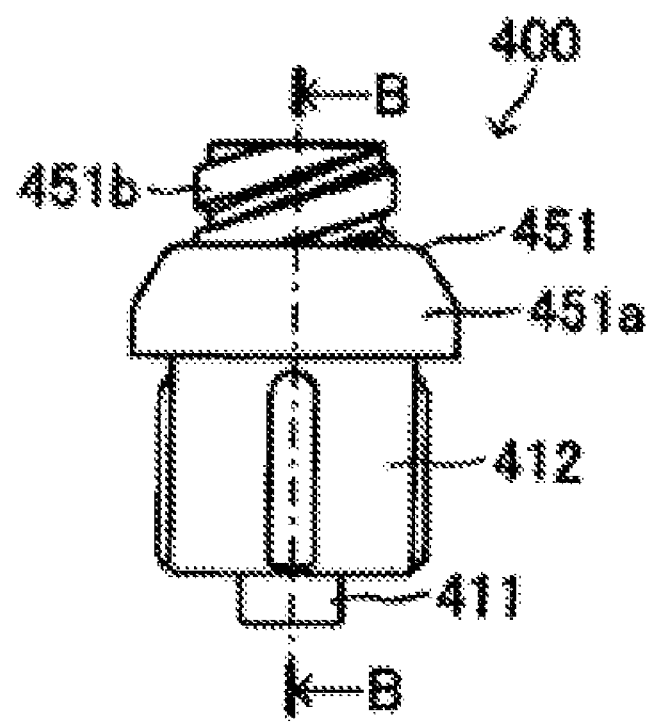
FIG. 17(a) is a front view of a connector in Embodiment 4 of the present invention.
Figure 17B:
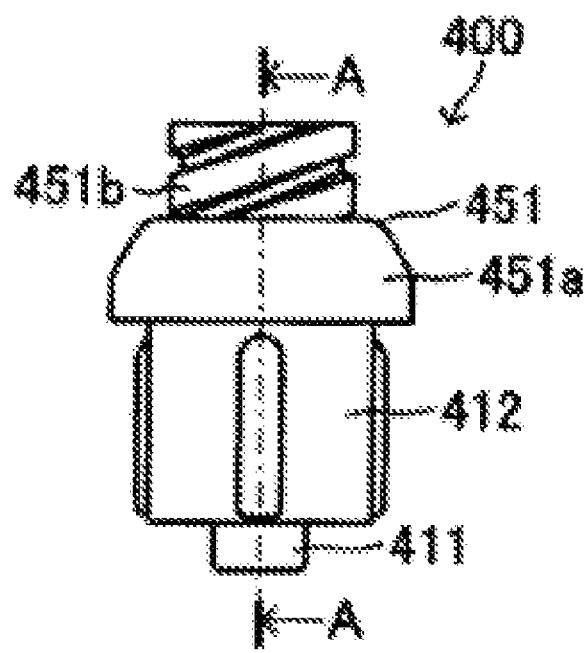
FIG. 17(b) is a side view of the connector in Embodiment 4 of the present invention.
Figure 17C:
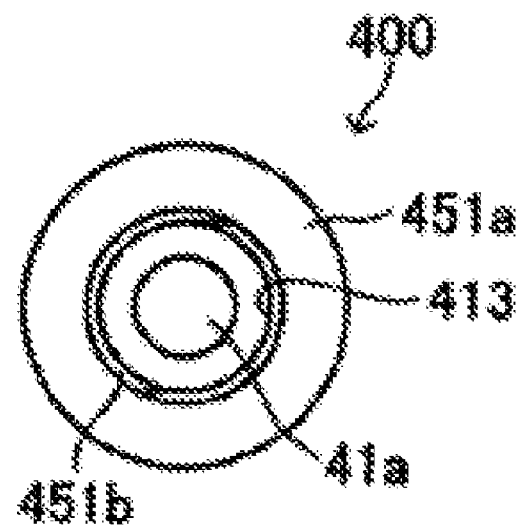
FIG. 17(c) is a plan view of the connector in Embodiment 4 of the present invention.
Figure 18A:
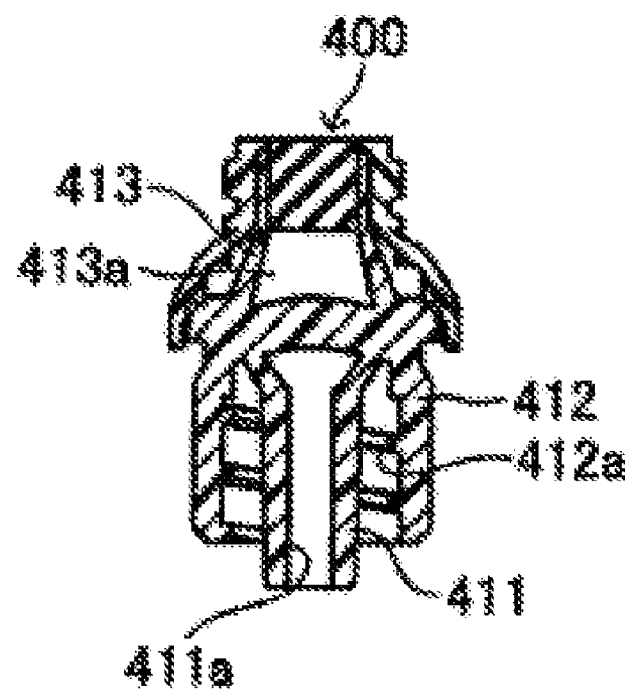
FIG. 18(a) is a cross sectional view of the connector taken across A-A of FIG. 17(b)
Figure 18B:
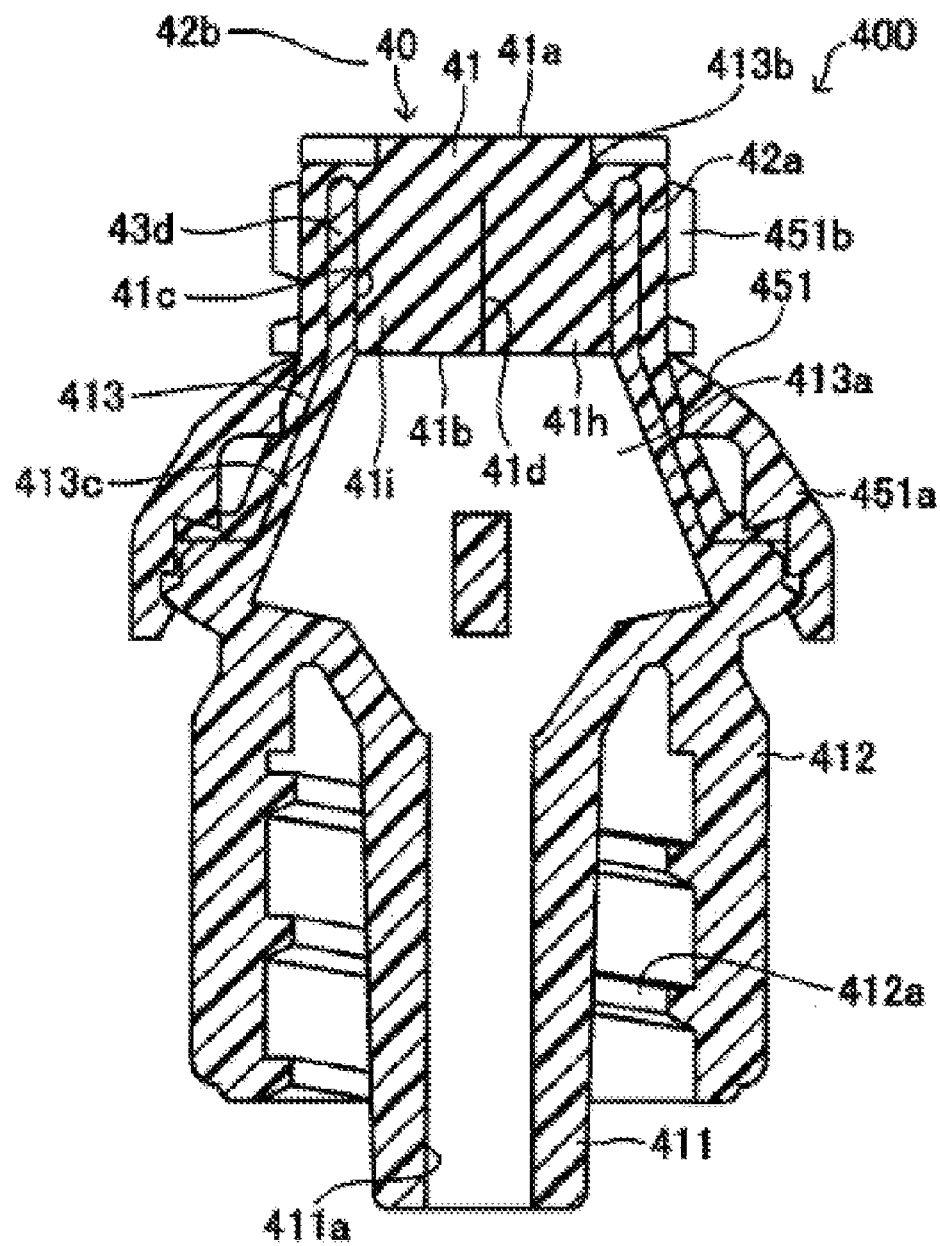
FIG. 18(b) is a cross sectional view of the connector taken across B-B of FIG. 17(a).

FIG. 17(a) is a front view of the connector in this embodiment. FIG. 17(b) is its side view, FIG. 17(c) is its plan view. FIG. 18(a) is a cross sectional view taken across A-A in FIG. 17(b). FIG. 18(b) is a cross sectional view taken across B-B in FIG. 17(a).

As can be seen from these figures, connector (400) of the present embodiment has housing (410). This housing (410) is composed of connecting tube portion (411), connecting tube cover portion (412), and connecting tube portion (413).

Said connecting tube portion (411) has a slender cylindrical shape, with connecting flow channel (411a) formed in it. This connecting tube portion (411) is connected to a tube or other tubular part. Also, connecting tube cover portion (412) is formed in a cylindrical shape to cover the outer periphery of connecting tube portion (411). Also, internal thread (412a) is formed on the inner wall of connecting tube cover portion (412). Said internal thread (412a) is screwed to the tube connected to connecting tube portion (411), and it thus fixes the tube. Connecting tube portion (413) is connected to the base end portion of connecting tube portion (411), and it has connecting space (413a) formed inside it. As shown in the figure, said connecting space (413a) is connected to connecting flow channel (411a) inside connecting tube portion (411). Here, connecting space (413a) corresponds to the flow space in the present invention.

As shown in FIG. 18(b), connecting tube portion (413) is composed of tapered portion (413c) having a tapered inner wall, and cylindrical portion (413d) that extends from the tip of tapered portion (413c) upward in a cylindrical shape as shown in the figure. Then, opening portion (413b) is formed on the tip of cylindrical portion (413d). Said tapered portion (413c) has connecting space (413a) formed inside it. Said connecting space (413a) is connected to connecting flow channel (411a) positioned in the lower portion as explained above.

On the outer periphery of connecting tube portion (413), cover (451) made of a plastic material is attached. Said cover (451) is composed of dome portion (451a) formed in a dome shape and outer threaded portion (451b) erected from the central portion of said dome portion (451a). Also, the upper end of outer threaded portion (451b) is open, and, from said opening portion, cylindrical portion (413d) of connecting tube portion (413) is inserted, and cover (451) is mounted on connecting tube portion (413). Also, on the inner periphery on the lower end of cover (451) as shown in the figure, a groove is formed along the circumferential direction. As this groove is engaged to tapered portion (413c), cover (451) is fixed on connecting tube portion (413). Also, an external thread is formed on the outer wall of outer threaded portion (451b). This external thread is for screwing of the Luer syringe portion of the syringe or the like for locking. The remaining features of the constitution, especially the constitution of valve member (40), are the same as those in said Embodiment 1, and the same part numbers are adopted, so that they will not be explained again.

For connector (400) in the present embodiment with the aforementioned constitution, first of all a tube or other tubular part is connected to connecting tube portion (411), and the tube is screwed and fixed by means of the internal thread of connecting tube cover portion (412). In this case, when no syringe is attached to valve member (40), as shown in FIG. 18(b), opening portion (413b) of connecting tube portion (413) is blocked liquid tight by main body portion (41) of valve member (40), so that it is in the closed state. Consequently, the tube attached to connecting tube portion (411) is blocked by valve member (40). As a result, even when liquid flows in the tube, the liquid does not leak out. Also, no impurity can enter from the outside via opening portion (413b) of connecting tube portion (413) into connecting space (413a).

When no medicine solution is fed from the side of connecting tube portion (413), the Luer syringe portion of the syringe is inserted into main body portion (41) of valve member (40), and the outer threaded portion is used for screwing and connecting to fix the Luer syringe portion. Then, the Luer syringe portion is used to press main body portion (41) into connecting space (413a), so that valve member (40) is opened. Here, the principle of the operation of opening of valve member (40) and connection of outer surface (41a) of main body portion (41) to third branching flow channel (313a) is the same as that of said Embodiment 1, so that it will not be explained in detail again. Consequently, the present invention may also be adopted in said connector.

While certain embodiments of the invention have been described in connection with a 3-way valve, it will be realized that the principles of the valve member (40) may be extended generally to other forms of connector, as shown by embodiments 3 and 4, particularly but not necessarily in respect of Luer connectors. The deployment of a closure such as valve member (40) on a female Luer connector provides a self-sealing closure which is automatically opened when a male connector is introduced into the female connector.

As indicated, the valve member (40) is formed from rubber-like material and may be natural or synthetic rubber. Additionally, the valve member may have a composite construction, being fabricated from more than one material. For example, the supporting arms may be made of a more resilient polymer while the internal portion may be more elastic.

At least one of the embodiments of the present invention provides a type of connector closure characterized by the fact that it has a valve member for which connection to the outside is reliably cut off when not in use, and leakage or bacterial reproduction can hardly take place.

In order to realize the aforementioned purpose, at least one embodiment of the present invention provides a type of connector closure characterized by the following facts: the connector has a housing, which has an opening portion opened to the outside and a connecting port connected to a tube and which has a flow channel space that allows the flow of liquid through said connecting port formed inside it, and a valve member attached to said opening portion, and is for feeding a liquid from outside into said flow channel space by turning said valve member ON/OFF; in this connector, said valve member has a main body portion that seals said opening portion liquid tight and can be moved to the side of said flow channel space under the pressing force from the outside, and a supporting portion, which is connected to said main body portion and is engaged to said housing, and which has an elastic force to act on said main body portion when said main body portion moves to the side of said flow channel space under the pressing force from the outside. Said main body portion has an outer surface facing the outside and the inner surface facing the flow channel space while said opening portion is blocked liquid tight; and, on said outer surface, a connecting surface is formed that is connected to said flow channel space when said main body portion is pressed into the side of said flow channel space under the pressing force from outside.

For the connector of at least one embodiment of the present invention with the aforementioned constitution, the valve member attached to the opening portion of the housing has a main body portion and a supporting portion. In addition, on said outer surface, a connecting surface is formed that is connected to said flow channel space when said main body portion is pressed into the side of said flow channel space under the pressing force from outside. Consequently, when the connecting surface is pressed in from the outside by the Luer syringe portion or other pressing member, the pressing member is pressed into said flow channel space together with the main body portion, and it is connected to the flow channel space. When the liquid to be fed from the pressing member is loaded in this state, the liquid loaded flows from the connecting surface into the flow channel space. In this way, feeding of the liquid is carried out.

On the other hand, when the pressing member is lifted from the connecting surface and the pressing force is released, under the elastic force received from the supporting portion, the main body portion returns to the original state (in the state in which it is not pressed into the flow channel space). As a result, connection of the flow channel space to the outside is cut off by the main body portion. In this way, for the valve member in the connector of at least one embodiment of the present invention, under the pressing force (pressure) applied from the outside, the main body portion is pressed into the flow channel space, and the outer surface of the main body portion is connected to the flow channel space. This system is different from the system in the prior art in which the outside and the flow channel space are connected to each other by a slit formed through the valve member. Consequently, there is no need to have the through slit as would be needed in the prior art. As a result, it is possible to prevent the valve member from becoming half open when not in use (when the Luer syringe portion is not inserted and no liquid is fed) caused by degradation of the through slit. Consequently, it is possible to cut off connection to the outside with high reliability when not in use, and the connector obtained has little chance of leakage or bacterial reproduction.

In at least one embodiment of the present invention, for the supporting portion, when the main body portion is pressed into the side of the flow channel space under the pressing force (pressure) of the pressing member, the main body portion is elastically supported in a state in which the main body portion hangs down from the side of the opening portion. As the pressing force (pressure) from the pressing member is eliminated, due to the elastic force generated by the supporting portion, the main body portion recovers the original state. As long as this function can be realized, any constitution may be adopted for the supporting portion. For example, one may adopt a system in which a spring is used as the supporting portion, and the spring is fixed on the main body portion. Also, one may also adopt a scheme in which the main body portion and the supporting portion are formed integrally as a rubber member or the like. In this way, the operation forming the valve member becomes simpler.

Also, it is undesirable that the supporting portion be attached without a gap around the entire circumference of the main body portion. This is because, as the supporting portion is attached without any gap around the entire circumference of the main body portion, when the main body portion is pressed into the flow channel space, there is no gap that can connect the outer surface and the flow channel space. Consequently, when the main body portion is pressed into the flow channel space, it is only required that a small gap for connecting the outer side portion and the flow channel space be there. This gap may be of a slit shape, or it may be a region not attached in the circumferential direction as the supporting portion is only partially attached in the circumferential direction of the main body portion. It is preferable that multiple supporting arms be mounted at balanced attachment positions (such as symmetrical positions) of the main body portion, and the multiple supporting arms are used as the supporting portion to hang the main body portion. By adopting said hanging type valve open/close structure, when the main body portion is pressed into the flow channel space, flow through the gaps of the various supporting arms to the outer surface and the flow channel space of the main body portion is possible.

As far as the main body portion is concerned, it is only required that it has an outer surface facing the outside and an inner surface facing the flow channel space, and that the opening portion can be blocked liquid tight. Any shape can be adopted for it. For example, it may have a round plate shape similar to that of the lid on a bottle of milk. As long as the aforementioned function can be displayed, it can be adopted. However, because it is necessary to block the opening portion liquid tight, it is preferable that the contact region with the opening portion be larger. For example, it may have the shape of a cylindrical rubber plug, with the outer surface and inner surface as the end surfaces. With said shape, its periphery can make a wide contact with the opening portion, so that a sufficient liquid tightness can be guaranteed.

As far as the outer surface of the main body portion is concerned, it is only required that it has a connecting surface that connects to the flow channel space when pressed by a pressing force (pressure) applied from outside into the flow channel space. It may have any shape. For example, the outer surface may be formed as a plane, and the entire surface is pressed into the flow channel space and connected to the flow channel space. In this case, the entirety of the outer surface becomes the connecting surface. Also, a groove may be formed on the outer surface with the plate shape, and when the outer surface is pressed into the flow channel space the groove is connected to said flow channel space. In this case, the surface of the groove becomes the connecting surface.

In addition in the aforementioned constitution, another characteristic feature of at least one embodiment of the present invention is as follows: on said main body portion, an inner slit is formed extending from said inner surface toward said outer surface while it opens to the inner surface (a cut is formed).

When the outer surface of the main body portion is pressed in by the Luer syringe portion of the syringe, a pressing force acts as a pressure in the direction toward the flow channel space side from the outside, that is, in the direction from the outer surface to the inner surface. On the other hand, when the main body portion is pressed by said pressing force toward the flow channel space side, a pulling force acts from the supporting portion that elastically supports the main body portion to have the main body portion return to its original position. This pulling force works from the flow channel space side toward the outside, that is, in the direction from the inner surface to the outer surface. Consequently, while the main body portion is acted on by a pressing force that presses from the outer surface toward the inner surface, it is also acted on by a pulling up force in the opposite direction. Consequently, a pair of forces consisting of these forces act on the main body portion.

Here, on the inner surface of the main body portion, when the acting point of the pulling up force is located on the outer periphery with respect to the acting point of the pressing force, due to the pair of forces, the inner surface of the main body portion is pulled from near the center (near the working point of the pressing force) toward near the outer periphery (the working point of the pulling up force).

In this case, according to at least one embodiment of the present invention, while opening on the inner surface (with a cut formed), an inner slit extending in the direction from the inner surface to the outer surface is formed. As a result, due to the aforementioned force, said inner slit is opened. Due to opening of the inner slit, a recess is formed on the position on the outer surface of the main body portion corresponding to the inner slit. As a portion of this recess is connected to the flow channel space, the liquid to be mixed and injected can flow at high efficiency from the recess into the flow channel space.

In this way, according to at least one embodiment of the present invention, not only is a connection made to the flow channel space by pressing the outer surface of the main body portion into the flow channel space, but also a pair of forces are applied to open the inner surface side of the main body portion, and a recess is formed on the outer surface in company with this operation with the recess connected to the flow channel space. Also, when the Luer syringe portion is pressed on the outer surface of the main body portion without forming said recess, the tip opening of the Luer syringe portion is pressed on the outer surface, and it may be impossible to feed the medicine solution from the Luer syringe portion. At this point, according to at least one embodiment of the present invention, due to the formation of said recess, a gap is formed between the tip opening of the Luer syringe portion and the outer surface, so that the medicine solution can be fed from the gap. In this way, at least one embodiment of the present invention can be adopted with a constitution that facilitates the patent application.

As to at least one embodiment of the present invention, as explained above, due to the pair of forces, a force acts from the center toward the outside on the inner surface of the main body portion. Consequently, on the inner surface, the acting point of the pulling up force from the supporting portion may be positioned in the outer radial direction from the acting point of the pressing force. Consequently, the portion where the supporting portion is connected to the main body portion (that is, the portion where the pulling up force acts on the main body portion) may be located on the outer periphery with respect to the portion where the pressing force acts on the main body portion (the portion where the main body portion receives the pressing force by a portion of the Luer syringe portion).

Also, the pulling up force from the supporting portion acts on the main body portion in at least two different directions. In this way, the pulling force from the center to the outside on the inner surface is dispersed into multiple directions, and the inner surface side of the main body portion can be opened more reliably. Consequently, the supporting portion may be connected to the main body portion in at least two or more different points. More preferably, one may adopt the scheme in which the portion of the main body portion receiving the pressing force is taken as the center, and the supporting portions are symmetrically connected to the main body portion. In this case, because the pressing force works nearly uniformly in the outer peripheral direction, the inner surface of the main body portion can be opened without deviation.

On the inner surface of the main body portion, it is undesirable that the inner slit be opened on the line segment connecting the acting point of the pressing force and the acting point of the pulling up force from the supporting portion, or in the direction parallel to said line segment. This is because said direction is the acting direction of the outward pulling force from the center of the inner surface, and when the slit is opened in said direction, the slit still cannot be opened. Consequently, the inner slit should be opened on the inner surface and in a direction different from said direction. It is most preferable that the inner slit be opened on the inner surface of the main body in the direction orthogonal to the line segment connecting the acting point of the pressing force and the acting point of the pulling up force, that is, in the direction perpendicular to the line segment connecting the pressing position when the main body is pressed by the pressing member and the pulling up position of the main body portion by the supporting member.

Also, it is preferable that the inner slit be formed to bisect the inner surface of the main body portion. When formed in this way, the inner slit can be easily opened by the outward pulling force from the center, and, at the same time, corresponding to the opening of the inner slit, the recess formed on the outer surface of the main body portion is formed as a groove along the inner slit. Consequently, the groove shaped recess works as a flow channel, and the liquid to be fed can flow along the groove shaped recess into the flow channel space. In this way, as the liquid to be fed flows along the groove shaped recess, the liquid can be fed at high efficiency from the outer surface without spilling.

Also, the following scheme is preferable: while an opening is formed on said outer surface (a cut is formed), an outer slit extending in the direction from said outer surface portion to the inner surface portion is formed. By means of said pair of forces, on the outer surface of the main body portion a force acts to fold to the inner side (central side). However, as said outer slit is formed, said force opens the outer slit, and the stress can be relaxed. Consequently, the reliability of the valve member can be improved and at the same time the service lifetime can be prolonged.

Also, on the outer surface of the main body portion, it is undesirable that the outer slit be opened on the line segment connecting the acting point of the pressing force and the acting point of the pulling up force from the supporting portion, or in the direction parallel to said line segment. The reason is as follows: said direction is the direction in which said force (the force for folding to the inner side) acts on the outer surface, and even when the slit is opened along this direction, the slit still cannot be opened. Consequently, the outer slit may be opened in a direction different from said direction on the inner surface. It is most preferable that the outer slit be opened in the direction perpendicular to the line segment that connects the acting point of the pressing force and the acting point of the pulling up force on the inner surface of the main body, that is in the direction perpendicular to the line segment that connects the pressing position when the main body is pressed by the pressing member and the pulling up position of the main body by the supporting member.

In this case, when the inner slit is formed, the forming surface of the outer slit and the forming surface of the inner slit may be set parallel to each other. In addition, the outer slit may be set near the portion where the supporting portion is mounted on the main body portion. Because the portion where the supporting portion is mounted on the main body portion is the portion where the stress is most concentrated. Consequently, by forming the outer slit near it, it is possible to effectively relax the stress concentration.

Having described the embodiments of the invention in detail, it will be apparent that modifications and variations are possible without departing from the scope of the invention defined in the appended claims.

When introducing elements of the present invention or the embodiments thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A closure for a connector having a housing, said housing having an opening portion opened to the outside, a connecting port connected to a tube and a flow channel space that allows flow of liquid through said connecting port, said closure comprising:
    a valve member for attachment to said opening portion and for allowing a liquid from outside to flow into said flow channel space after opening of said valve member, said valve member comprising
        a main body portion that seals said opening portion liquid tight and can be moved to the side of said flow channel space under the pressing force from the outside, said main body portion having an outer surface facing the outside and an inner surface facing the flow channel space while said opening portion is blocked liquid tight;

a supporting portion connected to said main body portion and engaged to said housing, the supporting portion having an elastic force that acts on said main body portion when said main body portion moves to the side of said flow channel space under the pressing force from the outside; and an inner slit formed in said main body portion from said inner surface toward said outer surface, the inner slit being spaced from the outer surface, wherein a connecting surface formed on said outer surface of the main body portion is connected to said flow channel space when said main body portion is pressed into the side of said flow channel space under the pressing force from outside.

2. The closure according to claim 1 wherein said inner slit is formed to bisect said inner surface.

3. The closure according to claim 1 wherein an outer slit is formed in said main body portion extending from said outer surface toward said inner surface.

4. The closure according to claim 1, wherein the closure is a part of a Luer connector.

5. The closure according to claim 4, wherein the closure is attached to a valve unit.

6. The closure according to claim 5, wherein the valve unit is a three-way valve unit.

7. A connector comprising:

a housing having an opening portion opened to the outside, a connecting port connected to a rube and a flow channel space that allows flow of liquid through said connecting port;

a valve member for attachment to said opening portion and for allowing a liquid from outside to flow into said flow channel space after opening of said valve member, said valve member comprising a main body portion that seals said opening portion liquid tight and can be moved to the side of said flow channel space under the pressing force from the outside, said main body portion having an outer surface facing the outside and an inner surface facing the flow channel space while said opening portion is blocked liquid tight;

a supporting portion connected to said main body portion and engaged to said housing, the supporting portion having an elastic force that acts on said main body portion when said main body portion moves to the side of said flow channel space under the pressing force from the outside; and an inner slit formed in said main body portion from said inner surface toward said outer surface, the inner slit being spaced from the outer surface, wherein a connecting surface formed on said outer surface of said main body portion is connected to said flow channel space when said main body portion is pressed into the side of said flow channel space under the pressing force from outside.

8. The connector according to claim 7 wherein said inner slit is formed to bisect said inner surface.

9. The connector according to claim 7 wherein an outer slit is formed in said main body portion extending from said outer surface toward said inner surface.

10. The connector according to claim 7, wherein the connector is a Luer connector.

11. The connector according to claim 7, wherein the connector is a valve unit.

12. The connector according to claim 11, wherein the valve unit is a three-way valve unit.

13. A fluid through-flow connector comprising:

at least one connection port, said connection port comprising a connection port housing having an inner surface defining an inner volume and an outer surface;

a sealing member having an inner portion extending within said inner volume and at least one outer portion extending externally of said housing, wherein said inner portion includes an inner slit extending from a lower surface of said inner portion, the inner slit being spaced from the outer surface, wherein said sealing member is of an elastically deformable material, wherein said sealing member is arranged such that it is deformable from a first closed state in which said sealing member is arranged in a fluid sealing configuration to a second open state in which said sealing member is arranged in a fluid non-sealing configuration and in which said inner portion is displaced into said inner volume and in which said at least one outer portion exerts a restoring force on said inner portion urging said inner portion to return to said first closed state, said deformation from said first closed state to said second open state being caused by the making of a connection to said connection port.

14. The connector according to claim 13 wherein said inner slit extends only partially between said lower surface and an upper surface of said sealing member.

15. The connector according to claim 14 wherein said sealing member further includes at least one outer slit extending from an upper surface of said inner portion.

16. The connector according to claim 15 wherein each of said inner slit and said at least one outer slit extend only partially between said upper surface and said lower surface.

17. The connector according to claim 13 wherein said sealing member comprises two said outer portions.

18. The connector according to claim 13 wherein said sealing member is secured to said housing by a cover.

19. The connector according to claim 13 wherein said inner surface comprises a substantially cylindrical upper region and a frusto-conical lower region.

20. The connector according to claim 13 wherein the connector is a Luer connector.

21. The connector according to claim 20 wherein the Luer connector is part of a valve system.

\* \* \* \* \*